United States Patent
Dae et al.

(10) Patent No.: US 7,172,586 B1
(45) Date of Patent: Feb. 6, 2007

(54) METHOD OF INOTROPIC TREATMENT OF CIRCULATORY FAILURE USING HYPOTHERMIA

(75) Inventors: Michael W. Dae, Belmont, CA (US); Paul M. Stull, San Mateo, CA (US)

(73) Assignee: Radiant Medical, Inc., Redwood City, CA (US)

(*) Notice: Subject to any disclaimer, the term of this patent is extended or adjusted under 35 U.S.C. 154(b) by 387 days.

(21) Appl. No.: 10/606,499

(22) Filed: Jun. 26, 2003

Related U.S. Application Data

(63) Continuation of application No. 09/938,851, filed on Aug. 24, 2001, now Pat. No. 6,607,517.

(51) Int. Cl.
*A61M 31/00* (2006.01)

(52) U.S. Cl. .......................... 604/500; 604/31; 607/106

(58) Field of Classification Search .................. 604/31, 604/6.13; 607/96–102, 104, 105, 106, 115, 607/116; 606/21, 27, 29, 31, 22
See application file for complete search history.

(56) References Cited

U.S. PATENT DOCUMENTS

| | | | | |
|---|---|---|---|---|
| 4,565,830 | A | | 1/1986 | Azuma .................. 514/553 |
| 5,082,831 | A | * | 1/1992 | Leaf et al. .................. 514/56 |
| 5,610,134 | A | | 3/1997 | Clark et al. .................. 514/2 |
| 5,700,283 | A | | 12/1997 | Salo .......................... 607/17 |
| 5,716,378 | A | * | 2/1998 | Minten ........................ 607/3 |
| 6,221,851 | B1 | | 4/2001 | Feldman ..................... 514/46 |
| 6,383,180 | B1 | * | 5/2002 | Lalonde et al. ............... 606/22 |
| 6,436,130 | B1 | * | 8/2002 | Philips et al. ............... 607/105 |

(Continued)

OTHER PUBLICATIONS

Ewy, Gordon A. M.D., FACC, "Intropic Infusions for Chronic Congestive Heart Failure", pp. 572-575, Journal of the American College of Cardiology, vol. 33, No. 2, 1999.

(Continued)

*Primary Examiner*—Manuel Mendez
(74) *Attorney, Agent, or Firm*—Robert D. Buyan; Stout, Uxa, Buyan & Mullins, LLP

(57) ABSTRACT

A method for treating cardiac failure such as congestive heart failure by application of hypothermia. Hypothermia may be applied by endovascular cooling using a heat exchange catheter circulating heat exchange fluid between an external heat exchanger controlled using temperature feedback from a temperature probe on or in the patient to cool the heart to a sufficiently low temperature for a sufficient length of time to increase cardiac output and improve the vascular condition of the patient. The patient may be maintained in the hypothermic condition for a period of time and is then re-warmed slowly and controllably. The endovascular temperature management may be controlled automatically in response to a temperature probe on the patient, and shivering while the patient is cool may be combated using surface warming and anti-shivering drugs. The method is applicable to treat congestive heart failure and may be used repeatedly on the same patient to restore that patient to adequate heart function when the vascular condition of that patient has become unacceptable. The method may be used to maintain a patient until a heart transplant becomes available. The method may be used to stabilize a patient's condition to allow needed surgery or intervention. The method may be used in conjunction with other treatments including drugs, balloon pumps, pacing devices and ventricular assist devices.

17 Claims, 12 Drawing Sheets

U.S. PATENT DOCUMENTS 6,478,029 B1 * 11/2002 Boyd et al. ............... 128/898
6,607,517 B1 * 8/2003 Dae et al. .................. 604/500
2002/0032473 A1 3/2002 Kushnir et al.

OTHER PUBLICATIONS

Toung, James B. M.D., and Moen, Elaine, K., M.D., "Outpatient Parenteral Inotropic Therapy for Advanced Heart Failure", The Journal of Heart and Lung Transplantation, vol. 19, No. 85, 2000.

http://www.texheartsurgeons.com/LVRsurgery.html, "Left Ventricular Reduction Surgery", Surgical Associates of Texas, 2000.

http://www.americanheart.org/Heart-and-Stroke-A-Z-Guide/htrans.html, "Heart Transplants and Statistics", American Heart Association, Inc., 2000.

National Heart, Lung, and Blood Institute Data Fact Sheet, "Congestive Heart Failure in the United States: A New Epidemic", pp. 1-6, Sep. 1996.

Blumenthal, D.K., "Cardiac Inotropic Drugs & the Treatment of Heart Failure", http://www.md.huji.ac.il/mirrors/netpharm/inotrope.htm, pp. 1-15.

* cited by examiner

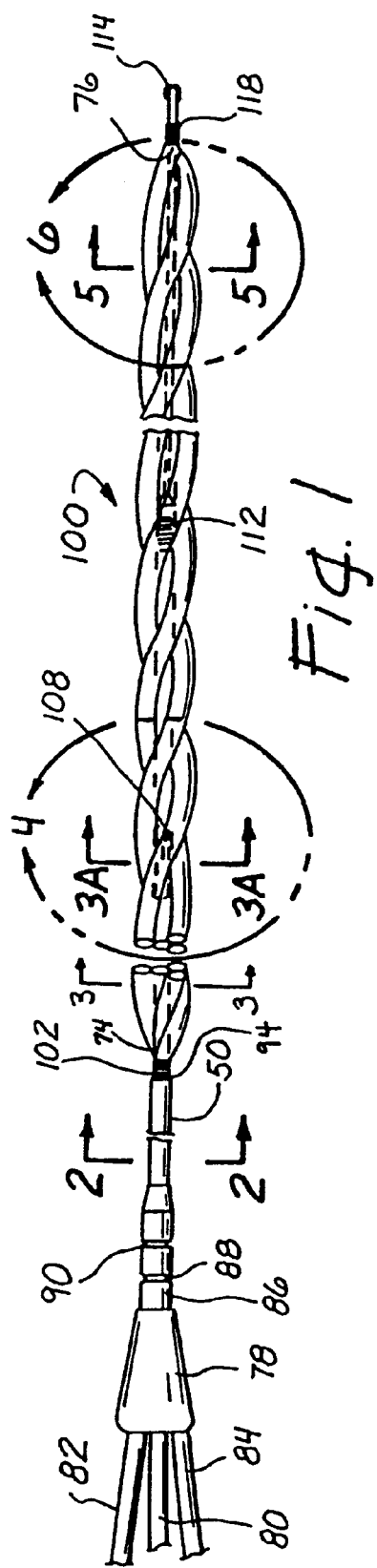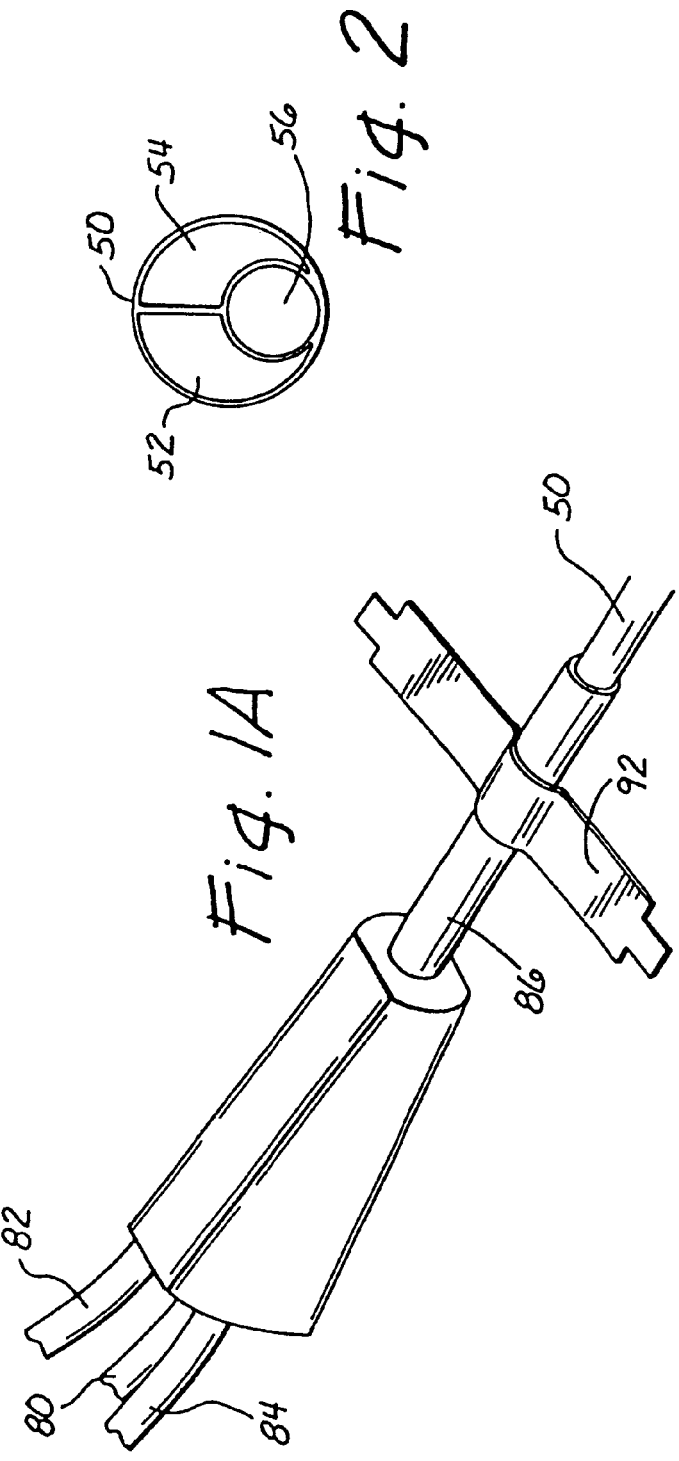

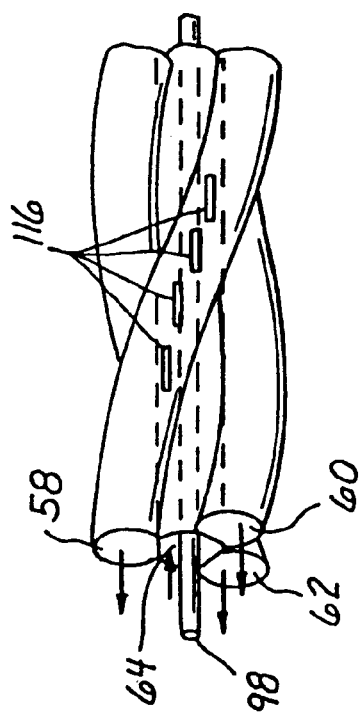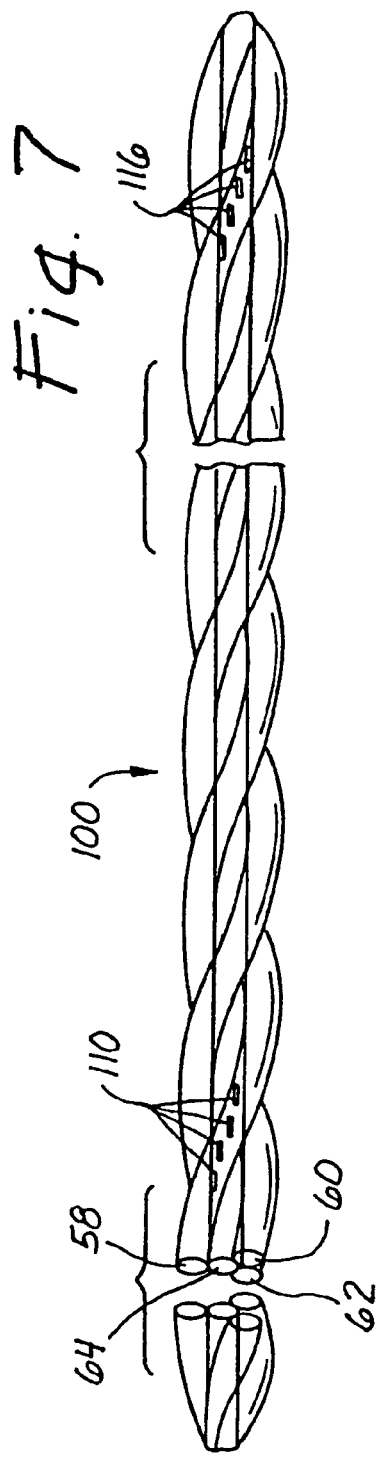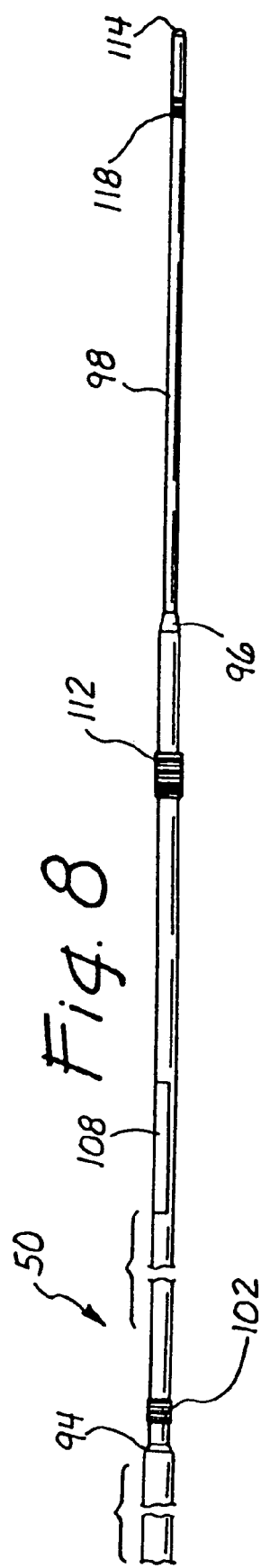

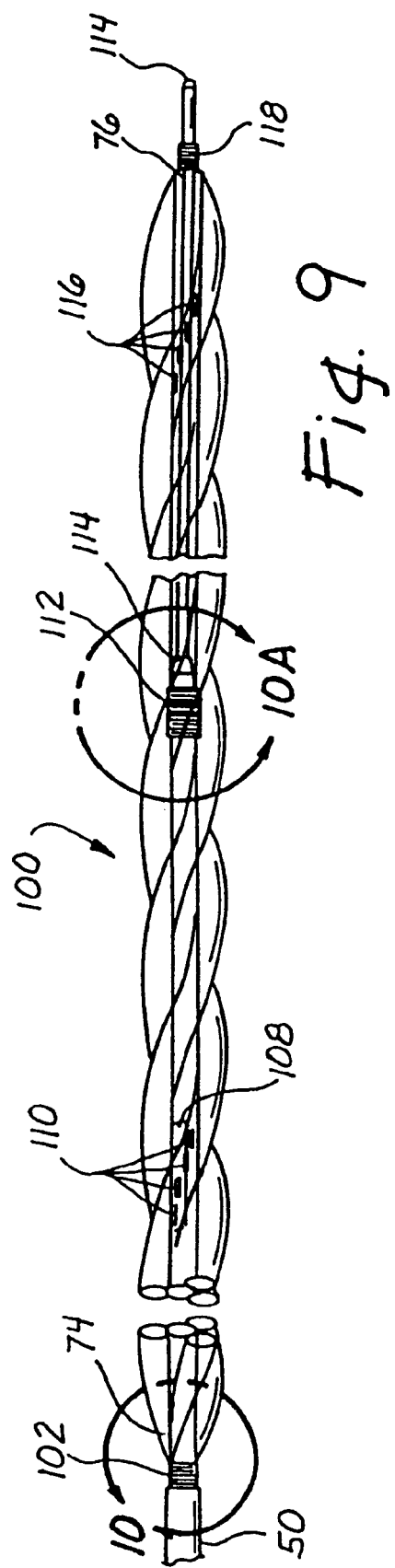

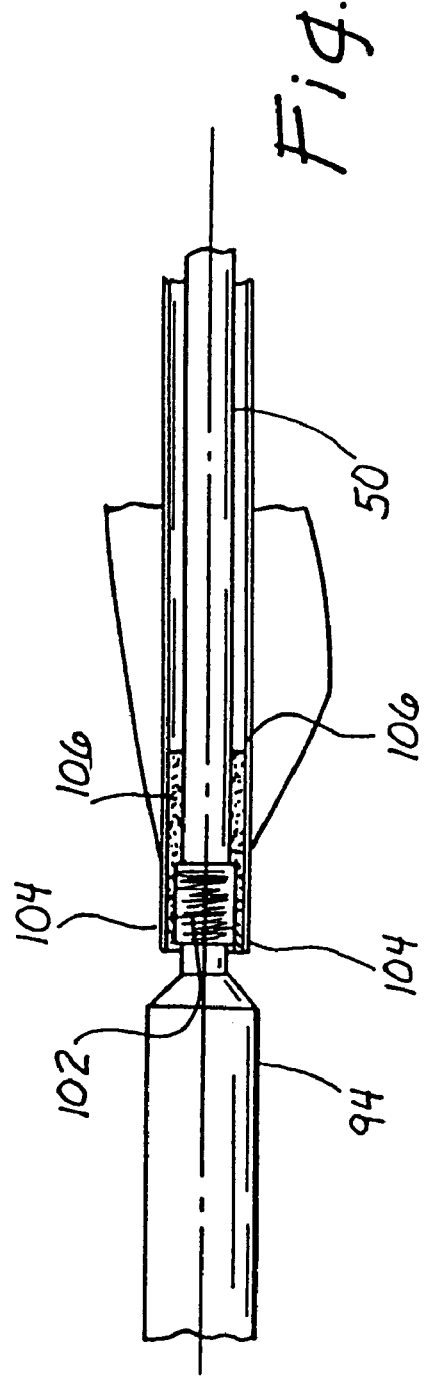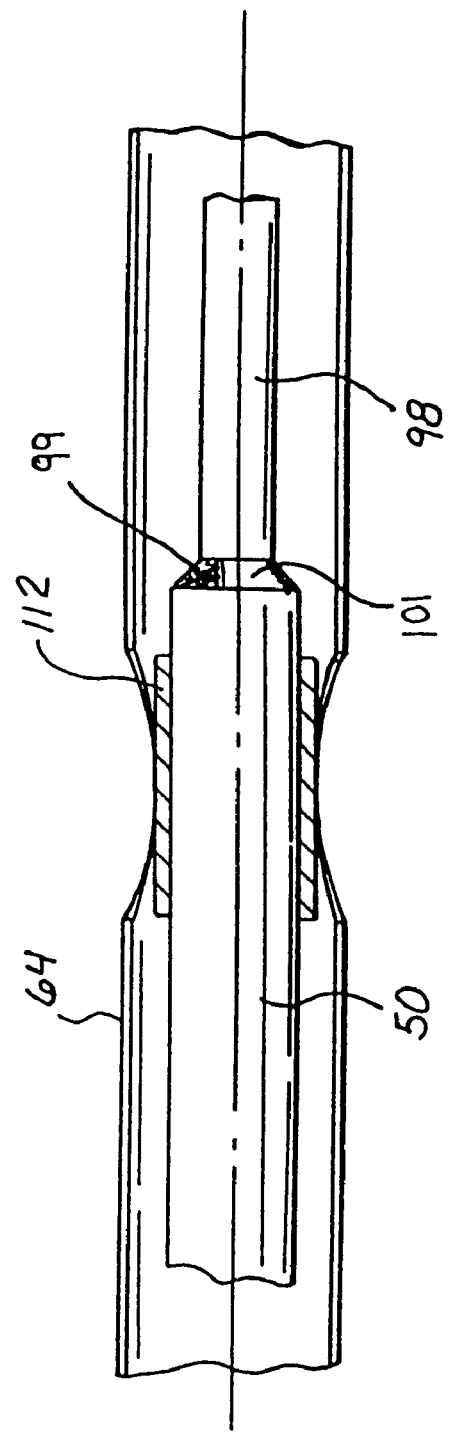
Fig. 10
Fig. 10A

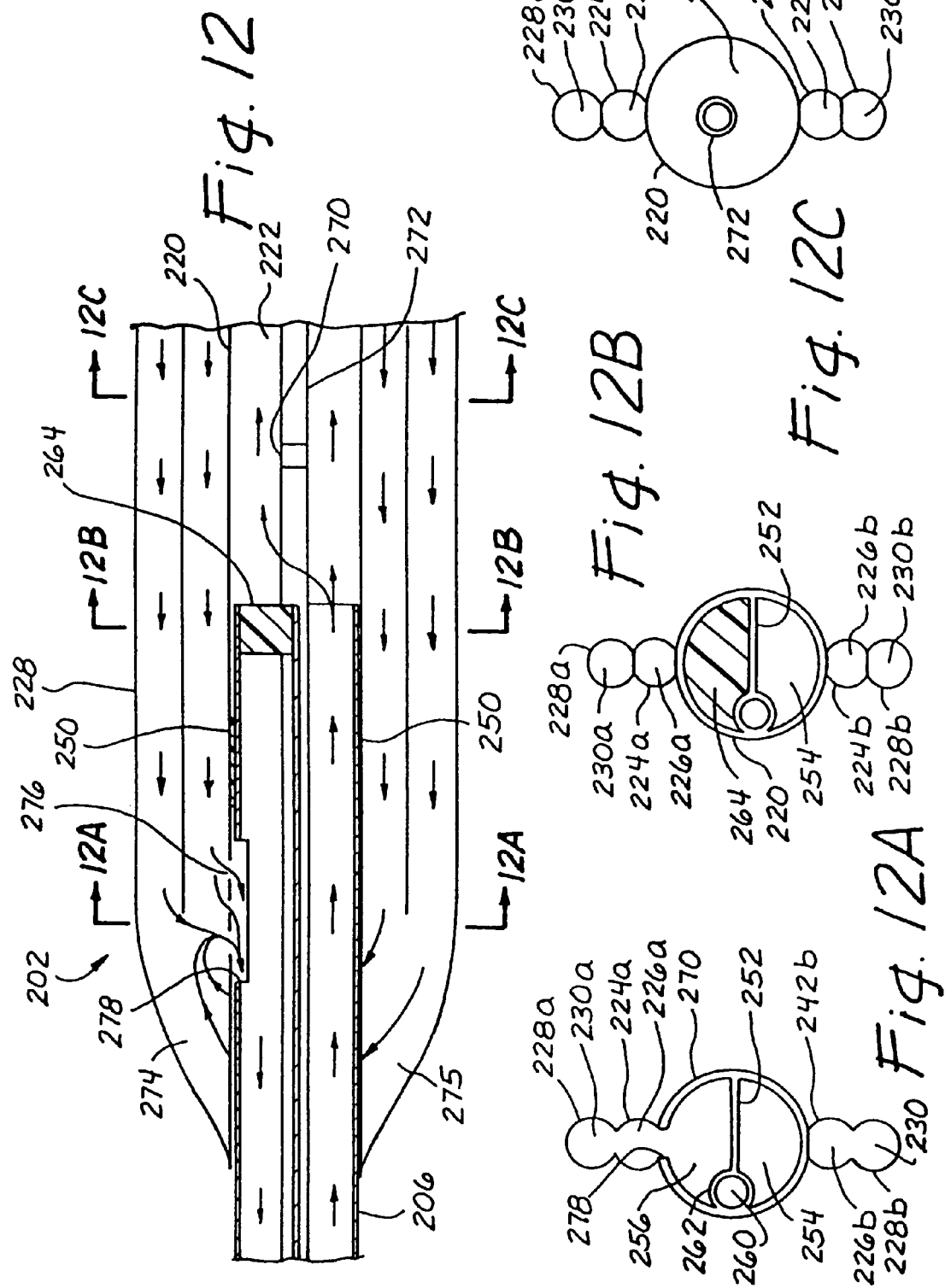

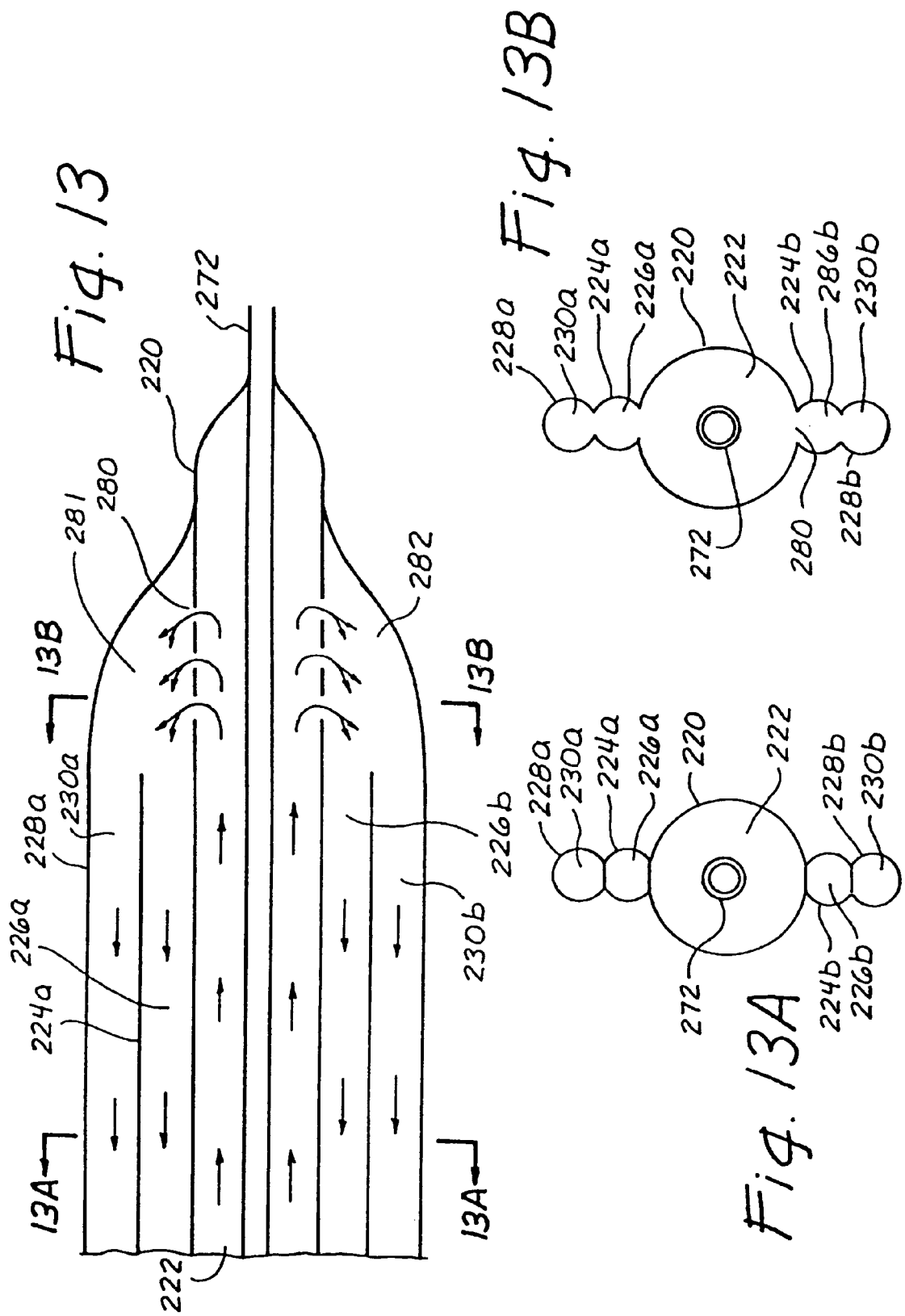

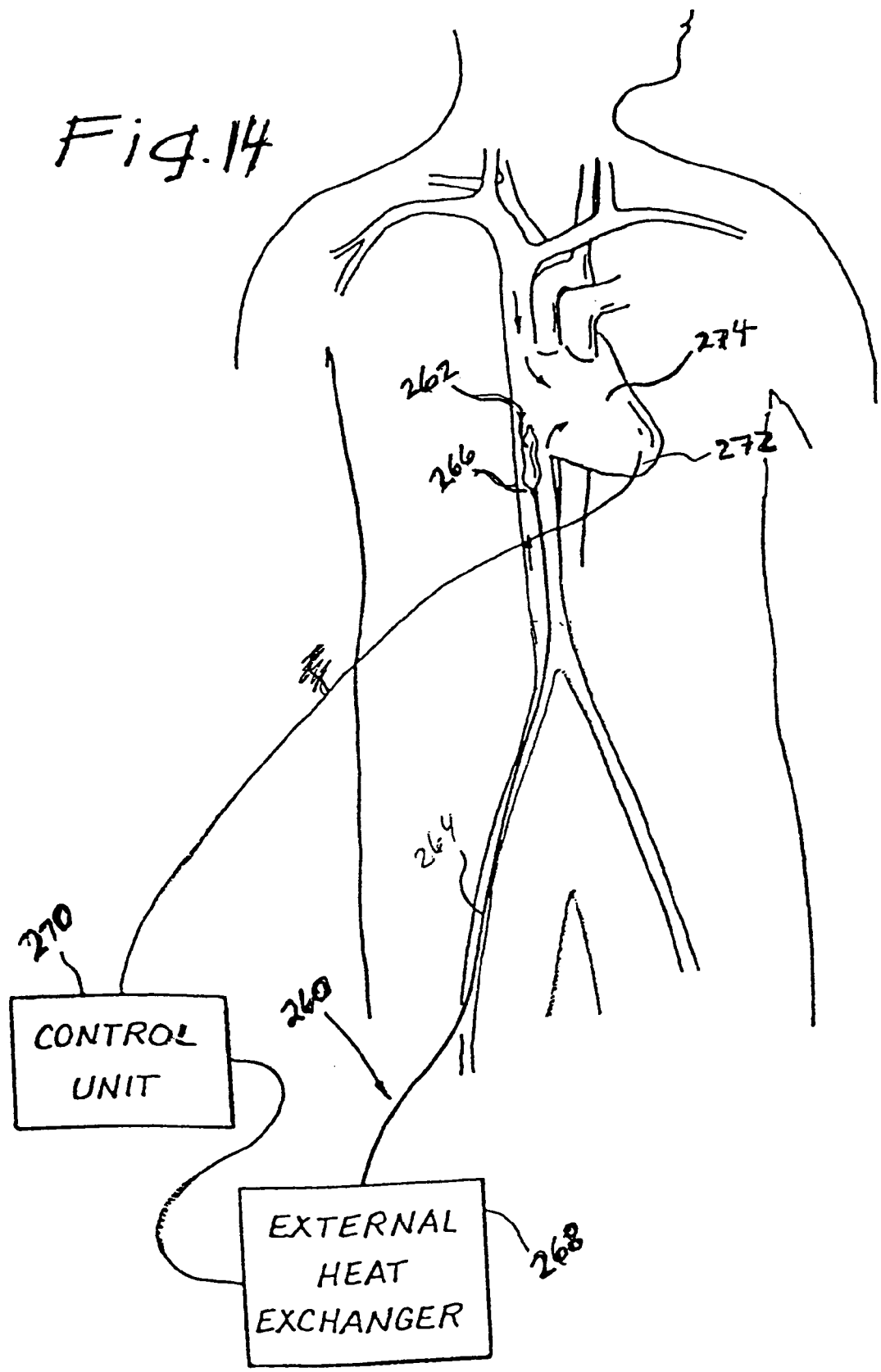

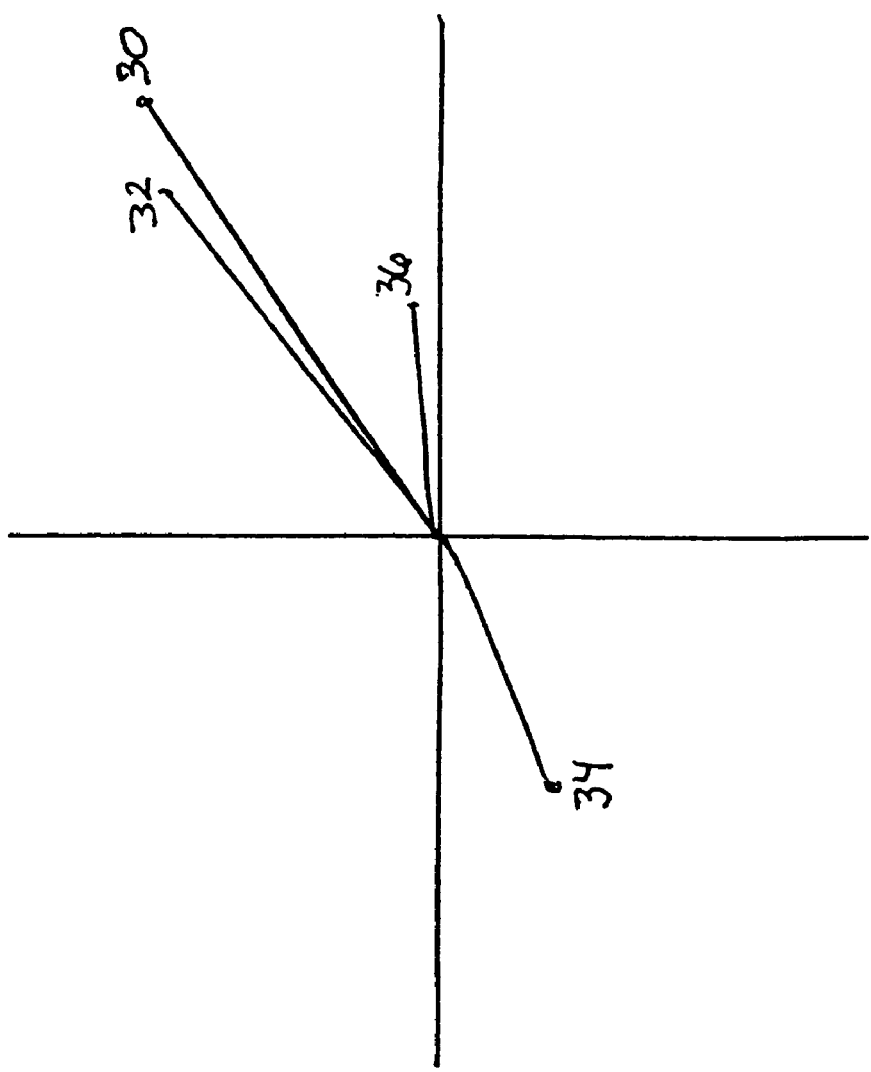

METHOD OF INOTROPIC TREATMENT OF CIRCULATORY FAILURE USING HYPOTHERMIA

This is a continuation of application Ser. No. 09/938,851 filed on Aug. 24, 2001, now U.S. Pat. No. 6,607,517, issued on Aug. 19, 2003.

FIELD OF THE INVENTION

This invention relates generally to methods for medical treatment and more particularly to the application of hypothermia by various means including by endovascular heat exchange to treat chronic heart disease. These methods find particular usefulness in treating congestive heart failure.

BACKGROUND OF THE INVENTION

Chronic cardiac failure may occur over a long period of time and may result from many root causes: diabetes, high blood pressure, clogged coronary arteries, and even acute events such as heart attacks. Whenever a heart has inadequate output, the resultant problems are legion and often systemic. The diseases is progressive; because of the inadequate supply of oxygen-rich blood to fuel the body's needs, people with heart failure often experience shortness of breath and uncommon fatigue with daily activities. Then as the condition progresses, the chambers of the heart—particularly the ventricles—become increasingly enlarged as the heart tries to compensate for the inefficiencies. Ultimately a complex process of damaging structural and functional changes to the heart result. The enlarged heart looses the ability to pump efficiently. There may be inadequate ability to handle venous return, leading to congested liver, water retention in the extremities and other problems of edema. There may be inadequate output from the left heart leading to congested lungs. There may be inadequate supply of oxygenated blood to various organs including the heart itself, and areas including the brain, leading to all the problems associated with hypoxia. There may be inadequate removal toxic metabolic waste products from organs or failure to clear drugs or toxic substances via the liver, leading to toxin-induced pathological conditions.

The condition of heart failure is complex and may be diagnosed by any one or a number of different criteria: the cardiac output may be low, generally considered below 2.5 liters per minute; the stroke volume of the heart may be low, for example below 25 cc; the ejection fraction of the sick heart may be below 40%; there may be echocardiographic findings of enlarged or improperly pumping hear; physical examinations including x-rays and stress testing may indicate cardiac failure; there may be cardiomegally; there may be increased left ventricular wall thickness and chamber dilation indicative of cardiac failure; there may be pulmonary edema, which with other symptoms and findings may indicate cardiac failure; there may be angiographic findings indicative of heart failure; and a diagnostic test of blood components, such as electrolytes or proteins may indicate heart failure. This lis is not exhaustive of the symptoms and findings that may help diagnose heart failure, but is offered to show the extent to which heart failure impacts the entire patient and may radically deteriorate the patient's life quality.

One common condition is congestive heart failure (CHF). CHF is one of the most serious health problems in the world. An estimated 4.8 million Americans alone have CHF. It is often the end stage of serious heart disease; half of those diagnosed with CHF will be dead within 5 years. An estimated 400,000 new case are diagnosed each year. It is the most common diagnosis in hospital patients age 65 years and older, with the disease affecting 10% of all those over the age of 70. The financial cost of treatment of CHF patients is over $17 billion a year. The human cost is beyond measure.

CHF is a complex clinical syndrome characterized by impaired ventricular performance, exercise intolerance, a high incidence of ventricular arrhythmias, and shortened life expectancy. It general, the heart is not pumping well enough to meet the body's metabolic demands and to provide adequate venous return. CHF is generally the result of a long clinical process. A general description of the downward spiral is: from normal heart function, to asymptomatic left ventricular (LV) dysfunction, to compensated CHF, to decompensated CHF and finally refractory CHF.

In the patient with asymptomatic left ventricular dysfunction, the abnormality in function is usually detectable by laboratory testing only. As the disease progresses, the patient develops symptoms such as mild exercise intolerance indicating inadequate cardiac output during stress. Milder forms of therapy are required at this point, such as diuretics, vasodilators and digoxin. The heart compensates by dilating to increase the volume of blood ejected per beat to increase cardiac output. Over time, the heart grows in size (myocardial hypertrophy) but also dilates to become more flaccid and less able to pump efficiently.

As the disease progresses, the structural changes become inadequate to successfully compensate, and the patient decompensates and becomes symptomatic at rest. Aggressive therapy is required at this point, consisting of diuretics, vasodilators and potent inotropic agents. These inotropic agents can lead to a transient improvement in hemodynamics, but may also accelerate the degenerative process in the heart, and increase mortality. Once the patient becomes unresponsive to inotropic therapy, a period of refractory CHF ensues. Treatment options are then generally limited to mechanical support (e.g. LV assist devices) or cardiac transplantation.

When the sufferer of CHF enters this final stage and the cardiac disease is so severe that he or she needs a heart transplant to survive for any length of time, the outlook is grim. According to the United Network for Organ Sharing (UNOS), more than 40,000 patients were waiting for a heart transplant as of February of 2000, and only 2,235 people received a donated heart in 2000. The vast majority of those needing a heart transplant will die waiting.

One method of increasing the likelihood that the patient will survive to receive a heart transplant is to treat the patient's heart with inotropic drugs or heart pacer to return it temporarily to an improved state and temporarily provide the patient's body with improved cardiac output. This treatment regime has the severe disadvantages set out below, and is not always available, but when available does provide a temporary improvement that might forestall death.

Inotropic drugs are drugs that increase muscle contractility, and in particular the contractility of the heart muscle. The drugs available include digitalis glycosides, available for almost 200 years to increase the force of contraction in both normal and failing heart muscles, but these have a very narrow therapeutic range and are limited by toxic side effects. The patient may develop tolerance and these drugs loose their effectiveness and the dose must be increased. Eventually they may not be effective at all.

Another treatment for those with decompensated congestive heart failure is the administration of the inotropic drugs milrinone or dobutamine. These drugs cause the heart to pump more vigorously and perhaps more effectively and to lead to improved over-all condition of the patient, temporarily, However, chronic administration of these inotropic drugs generally leads to worsened long term prognosis and increased mortality rates. It has been postulated that the increase in metabolic activity leads to the buildup of potentially harmful metabolic by-products and perhaps also artificially overrides the auto protective effect of hibernation of heart tissue. In any event, the administration of these drugs may lead to long term heart muscle deterioration and long term increased mortality. There may also be more immediate dangers: patient's who receive inotropic drugs and show clinical improvement over the short term often have symptomatic and hemodynamic rebound leading to worsened heart failure during or shortly after being weaned from the inotropic drugs. As a result, these inotropic agents are only indicated for short-term intravenous administration in CHF patients who can be closely monitored and who have not responded well to digitalis, diuretics or vasodilators.

These intermittent periods of artificially increased heart output by drug therapy are sometimes referred to as drug holidays, that is the body is provided with a short term increase in cardiac output in order to maintain the patient until long term treatment is available. Refractory congestive heart failure is such a serious and dangerous problem that even such desperate measures may be justified. Several of these drug holidays may well be needed to ensure survival while a congestive heart failure patient waits for a suitable heart transplant donor. The short term improvement may be worthwhile to buy some time before the condition is once again grave and life threatening.

As with inotropic drugs, treatment with a heart pacer may lead to improvement in the short term, but the patient's condition generally degenerates again over time and the patient may suffer long term cardiac damage or even death due to the artificial stimulation of the heart muscle. Nonetheless, the administration of heart pacer therapy is still sometimes applied to hemodynamically unstable patients to provide support until more effective long term therapy (e.g. heart transplant) can be supplied. However, some method of achieving the short term benefits of inotropic therapy without the attendant long term disadvantages of the drugs or the pacer would be a great benefit.

Sometimes the patient's condition, due to CHF or other cardiac failure, is so poor that the patient is not a candidate for needed treatment. This may be the case, for example, if the patient is in such unstable hemodynamic condition that he or she is not a candidate for needed revascularization intervention such as percutaneous cardiac intervention (PCI), usually angioplasty, or by pass surgery due to the risk of death. It is rather ironic that the very condition that needs to be corrected, cardiac insufficiency, causes the patient to be so unstable that he or she is not eligible for treatment. Some method to achieve short-term stabilization is needed to allow application of the therapy, and some method without the long term disadvantages of the drug treatment mentioned above would be highly desirable.

Sometimes a post-operative patient has a heart that is not recovering, and the failure of the heart to pump properly makes post operative recovery impossible. Because of patient condition, other drugs being used or already in the patient's system, or other factors, the patient may not respond to or may not be eligible to receive inotropic drugs or mechanical pacing. In such a situation some other option would be of great value.

SUMMARY OF THE INVENTION

Mild hypothermia has been shown to both increase the contractility of the heart muscle and to reduce its metabolic requirements. Indeed, if the hypothermia is systemic, the metabolic demands of the entire body are generally reduced, so that the demands placed on the heart may be reduced. The present invention provides a method for treating the heart by application of mild hypothermia to increase the heart output and thus improve the overall condition of the patient. In general, the method comprises the steps of a) inducing hypothermia in the patient suffering from or in imminent danger of suffering form insufficient cardiac output; and b) maintaining the patient in the hypothermic condition for a sufficient time to provide a helpful amount of improved cardiac output. This method will also generally include the application of effective anti-shivering mechanisms. The method may also include the controlled re-warming of the patient.

Hypothermia is preferably induced by removing heat from the patient with a heat exchange apparatus. The heat exchange apparatus may be, for example a heat exchange catheter with a heat exchange region placed in the vasculature of the patient so that it directly exchanges heat with the blood flowing over the heat exchange region. Alternatively it may be a heat exchange catheter having a heat exchange region placed in the esophagus of a patient and exchange heat with blood with blood in the esophageal wall, or less directly, in the aorta through the esophageal and aortic walls. It may be a heat exchange catheter placed directly within the stomach. It may even be an enhanced method of cooling blood through the skin of the patient, as with a cooling blanket, cooling patch, or cooling tent, provided that whatever heat exchange method is used is fast and efficient enough to induce hypothermia sufficient to be therapeutic for the treatment of congestive heart failure and the user is able to control the shivering of the patient.

Patients may be given these hypothermic heart "holidays" for periods of 3 hours, 12 hours, or even up to three days depending on the individual patient's condition and needs. Since merely cooling a patient is fairly benign and the advantages may be quite dramatic, long lengths of hypothermic administration may be administered. When the patient is placed in a hypothermic condition, 1° C. or more below normothermic, and the output of the heart increases, the overall condition of the patient improves significantly and the patient's heart may receive sufficient additional blood and have a temporarily decreased metabolic need and decreased metabolic waste products so that it is able to recover to a healthier state and may even experience a reversal of heart damage as a result.

The danger of shivering is present whenever a patient is cooled below that patient's shivering threshold, which in humans is generally about 35.5° C. When inducing hypothermia below the shivering threshold, it is very important to control the shivering response. That response is so profound that it generates enough metabolic heat to overpower most cooling mechanisms, perhaps by as much as 200–600% over resting metabolic heat production (which also increases oxygen consumption by a similar amount, and generates a similar amount of potentially harmful metabolic by-products). In addition, the violent muscular activity that constitutes shivering is very stressful and generally very harmful to the patient suffering from congestive heart failure. Thus it is of great importance that shivering be avoided. This may be accomplished by the administration of certain drugs, and by the application of a warm blanket over the skin of the patient being cooled, and in many cases, both application of anti-shivering drugs and the application of a warming blanket. As can be seen, the application of surface cooling tends to exclude the possibility of application of a warming blanket, so for applications of hypothermia below the shivering threshold, generally endovascular hypothermia is preferable.

Once the patient has received the intended length of hypothermic treatment, the same heat exchanger used to induce the hypothermia may be used to re-warm the patient. This re-warming is generally a very slow and controlled re-warming. If the endovascular heat exchange catheter is under the automatic control of an external controller, perhaps in response to a temperature probe sensing the temperature of the patient, then the re-warming can be automatically started and the rate of re-warming controlled.

A second situation where this invention of using the application of mild hypothermia (32° C.–35° C.) to treat congestive heart failure is when a patient's medical condition is too unstable because of congestive heart failure to allow treatment by reperfusion therapy or surgery. In these cases, the invention may be applied by a) cooling the patient to achieve mild hypothermia of the patient; b) monitoring the patient's condition until the patient is sufficiently stable to permit the intervention or surgery; c) performing the intervention or surgery while the patient is maintained in a mildly hypothermic state; d) re-warming the patient in a controlled manner. A sensor of some patient parameter, such as pulse rate, oxygen consumption, blood flow, blood pressure or some combination of factors may be monitored, directly or automatically, to signal when the patient's condition is appropriate for intervention or surgery. In this case, as when the hypothermia is applied as a therapy for congestive heart failure without intervention or surgery, the cooling and subsequent re-warming may be under direct or under automatic control based on feedback from the patient.

Further aspects and particulars of the present invention will become apparent to those of skill in the art upon reading and understanding of the detailed description and examples set forth herebelow.

DETAILED DESCRIPTION OF THE DRAWINGS

FIG. 1 is a perspective drawing of an embodiment of the catheter of the invention.

FIG. 1A is a perspective drawing of an alternative tie-down at the proximal end of the catheter shown in FIG. 1.

FIG. 2 is a cross-sectional drawing of the shaft of the catheter taken along the line 2—2 in FIG. 1.

FIG. 6 is a perspective drawing of a segment of the heat exchange region of the catheter within the circle 6—6 in FIG. 1.

FIG. 7 is a perspective drawing of the multi-lobed balloon of one embodiment of the invention.

FIG. 8 is a perspective drawing of the distal portion of the shaft of one embodiment of the invention.

FIG. 9 is a perspective drawing, partially in ghost, of the heat exchange region formed by the shaft and multi-lobed balloon of FIGS. 7 and 8.

FIG. 10 is an expanded view of the attachment of the central lumen of the balloon to the shaft of the catheter of FIG. 9 showing the region within the circle 10—10 in FIG. 9.

FIG. 10A is an expanded view of the plug between the shaft and the central lumen of the balloon of the catheter of FIG. 9 showing the region within the circle 10A—10A in FIG. 9.

FIG. 12 is a sectional view of the proximal portion of the heat exchange region of one embodiment of the invention.

FIG. 12A is a cross-sectional view of a portion of the heat exchange region taken along the line 12A—12A of FIG. 12.

FIG. 12B is a cross-sectional view of a portion of the heat exchange region taken along the line 12B—12B of FIG. 12.

FIG. 12C is a cross-sectional view of a portion of the heat exchange region taken along the line 12C—12C of FIG. 12.

FIG. 13 is a sectional view of the distal portion of the heat exchange region of one embodiment of a catheter of use in the invention.

FIG. 13A is a cross-sectional view of a portion of the heat exchange region taken through line 13A—13A of FIG. 13.

FIG. 13B is a cross-sectional view of a portion of the heat exchange region taken through line 13B—13B FIG. 13.

FIG. 14 is a depiction of the catheter in place in a patient with a controller controlling the heat exchange catheter for practicing the invention.

FIG. 17

FIG. 17 is a chart showing heart oxygen metabolism when stimulated by various agents.

DETAILED DESCRIPTION

In a patient suffering from circulatory failure including congestive heart failure, inducing hypothermia has the dual advantage of increasing the contractility of the cardiac muscle cells, similar to an inotropic drug, while at the same time reducing the metabolic oxygen requirements of those same muscle cells.

Circulatory failure occurs when the heart has inadequate output to handle venous return and to supply sufficient blood circulation to supply needed blood to the body. It includes congestive heart failure, heart insufficiency after surgery, and includes cardiac insufficiency for various reasons, which creates such a high risk of death that the patient is ineligible for intervention or surgery.

Figure 16:
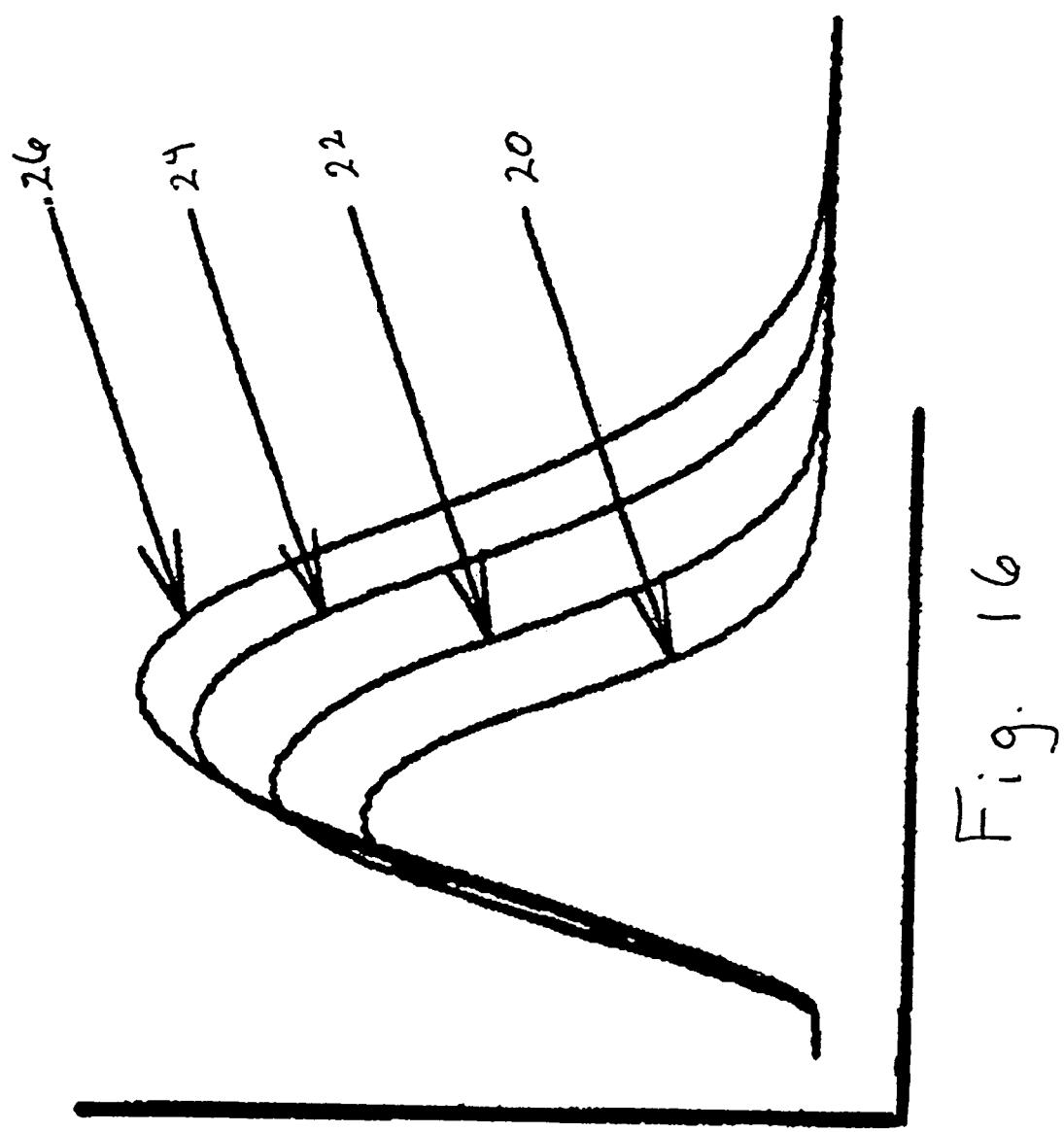
FIG. 16 is a chart of muscle cell contractility at various temperatures.

The effect of hypothermia on the demands and contractility of a cardiac muscle cells in vitro is shown in the diagram of FIG. 16. An increase in the vertical direction is an increase in contractility; an increase in the horizontal direction is an increase in time. At 20, the highest temperature, normothermia (37° C.) the muscle cell shows the least strength of contraction (lowest peak) and sustains that contracted state for the least amount of time (shortest curve). As the temperature decreases to 35° C., 22, to 33° C., 24 or to 31° C., 26 the strength of the contraction becomes more vigorous and is sustained for a longer time. The in vivo response of the heart organ reflects this; the cardiac output of a heart during hypothermia actually goes up while the heart rate goes down, a clear indication that the output per beat is increased.

Surprisingly, the amount of oxygen consumption and generally the metabolic requirements of the heart muscle is reduced by hypothermia at the same time that the cardiac output is improved. Inotropic drugs, on the other hand, tend to increase the metabolism of oxygen significantly if they increase the strength of the heart contractions. FIG. 17 illustrates the effect of some common inotropic agents, epeniferin 30 and calcium 32 where the administration of the agent showed an increase in contraction strength of the heart when administered that agent. In both those cases, the increase in contractility was accompanied with a very large increase in oxygen metabolism. In both those cases, the increase in contractility was accompanied with a very large increase in oxygen consumption. The administration of proponol 34 resulted in a decrease in oxygen metabolism; however there was also a significant decrease in strength of contraction. Paradoxically, with hypothermia 36 an increase in strength of contraction was accompanied by almost no increase oxygen metabolized.

The dramatic advantage of hypothermia for a patient suffering heart failure is captured by this invention. In fact, if the hypothermia delivered is systemic, there is even a third advantage; the metabolic requirements and waste products of the entire body are reduced, thus reducing the overall demands on the heart.

The method of this invention also sometimes involves preventing the patient from shivering by the application of an effective anti-shivering mechanism. That may involve the application of a warming blanket and various anti-shivering drugs, alone but usually in combination.

The method may also be practiced with automatic control over the heat exchange mechanism that is inducing and maintaining hypothermia. A temperature probe that senses the temperature of the patient provides a signal to an automatic control unit that, in response to that signal, controls the hypothermic state of the patient.

The general method of the invention comprises the steps of a) diagnosing a patient suffering or in imminent danger of suffering congestive heart failure; b) inducing hypothermia in the patient suffering from congestive heart failure or in danger of imminent suffering of congestive heart failure; c) maintaining the patient in the hypothermic condition for a sufficient time to provide a helpful amount of improved vascular output. The method may additionally include the steps of d) administering an effective anti-shivering agent, e) automatically controlling the patient's temperature using feedback from a temperature probe on or in the patient and f) re-warming the patient, perhaps at a very slow and controlled rate.

More specifically, the patient may be cooled by endovascular cooling (described in greater detail below) to a temperature between 32° C. and 36° C., maintained at that cooled temperature for a period of three hours, six hours, or even a day or more, and then re-warmed to normothermia, generally 36.5° C. to 37° C. Generally the warming is slow and controlled, sometimes as slow as 0.2° C./hr.

The patient's temperature may be under the control of an automatic temperature control system that may be governed by a signal from a temperature probe in or on the patient's heart, esophagus, blood stream, tympanic membrane, skin, or other area that will deliver a signal that is representative of the patient's heart temperature. The probe is connected, for example by electrical connection, to a controller that regulates the temperature of the patient in response to the measured temperature.

When the patient's temperature is below the shivering threshold, an anti-shivering mechanism is sometimes employed which may include a warming blanket, drugs, or some combination of both. This anti-shivering regime is generally started before the patient is cooled below the shivering threshold so that shivering never begins.

Induction of Hypothermia

Hypothermia may be induced by any means fast and efficient enough to cool the patient without undue stress, but preferably is induced by placing an endovascular heat exchange catheter in the patient's bloodstream and cooling the blood flowing over the catheter to cool the patient. The method in general is described in U.S. Pat. No. 6,110,168 to Ginsburg. Various catheters for achieving the endovascular cooling are described in U.S. Pat. No. 5,486,208 to Ginsburg, PCT publication WO OO/10494 to Machold et al., U.S. Pat. No. 6,264,679 to Keller et al., and U.S. application Ser. No. 09/777,612. Other less desirable endovascular cooling catheters may be employed to practice this patented method, for example U.S. Pat. No. 3,425,484 to Dato, U.S. Pat. No. 5,957,963 to Dobak III, U.S. Pat. No. 6,126,684 to Gobin, et al. and U.S. Pat. No. 5,531,776 to Ward et al. provided that they are able to provide adequate hypothermia to the diseased heart.

An advantageous method of inducing hypothermia uses temperature management, with a catheter that circulates heat exchange fluid through a heat exchange region that is a balloon, and circulating the heat exchange fluid through an external heat exchanger to adjust the temperature of the heat exchange fluid and then recirculating it through the balloon. This circulation is continuous, preferably in a closed circuit, exchanging heat from the blood into the heat exchange fluid, and then out of the heat exchange fluid in the external heat exchanger for a sufficient length of time to cool the patient to achieve the desired advantages of this invention.

Advantageous endovascular heat exchange catheter systems are described in reference to FIGS. 1 through 13B. Referring to FIGS. 1 through 10A, in one embodiment, the catheter is comprised of a shaft 50 with a heat exchange region 100 thereon. The shaft has two roughly parallel lumens running through the proximal shaft, an inflow lumen 52 and an outflow lumen 54. The shaft generally also comprises a working lumen 56 running therethrough for the insertion of a guide wire, or the application of drugs, radiographic dye, or the like to the distal end of the catheter. The heat exchange region comprises a four-lumen balloon, with three outer lumens 58, 60, 62 disposed around an inner lumen 64 in a helical pattern. In the particular embodiment shown, the balloon preferably makes one full rotation about the inner lumen 64 for each 2 to 4 inches of length. All four lumens 58, 60, 62 and 64 are thin walled balloons and each outer lumen 58, 60, 62 shares a common thin wall segment 66, 68, 70 with the inner lumen. The balloon is approximately twenty-five centimeters long, and when inflated has an outer circumference 72 of approximately 0.328 in. When deflated, the profile is generally about 9 French (3 French is 1 mm in diameter). When the balloon portion is installed on the shaft, both the proximal end 74 of the balloon and the distal end 76 of the balloon are sealed around the shaft in fluid tight seals, as described more fully herebelow. Heat exchange fluid may be directed in through the inflow lumen, return through the outer lobes of the balloon in heat exchange proximity with blood flowing over the outside of the balloon, and then out through the outflow lumens, as will be described in greater detail below.

The catheter is attached at its proximal end to a hub 78. At the hub, the guide wire lumen 56 communicates with a guide wire port 80, the inflow lumen 52 is in fluid communication with an inflow port 82, and the outflow lumen 54 is in communication with an outflow port 84. Attached at the hub and surrounding the proximal shaft is a length of strain relief tubing 86 which may be, for example, a length of heat shrink tubing. The strain relief tubing may be provided with suture tie-downs 88, 90. Alternatively, a butterfly tie-down 92 may be provided. (See FIG. 1A).

Between the strain relief tubing 86 and the proximal end of the balloon 74, the shaft 50 is extruded with an outer diameter of about 0.118 inches. The internal configuration is as shown in cross-section in FIG. 2. Immediately proximal of the balloon attachment 74, the shaft is necked down 94. The outer diameter of the shaft is reduced to about 0.100 to 0.110 inches, but the internal configuration with the three lumens is maintained. Compare, for example, the shaft cross-section of FIG. 2 with the cross-section of the shaft shown in FIG. 3. This length of reduced diameter shaft remains at approximately constant diameter of about 0.100 to 0.110 inches between the necked down location at 94 and a distal location 96 where the outflow lumen is sealed and the guide wire extension tube 98 is attached as will be described.

At the necked down location 94, a proximal balloon marker band 102 is attached around the shaft. The marker band is a radiopaque material such as a platinum or gold band or radiopaque paint, and is useful for locating the proximal end of the balloon by means of fluoroscopy while the catheter is within the body of the patient.

At the location marked by the marker band, all four lobes of the balloon are reduced down and fastened around the inner member 67 in a fluid-tight seal. This may be accomplished by folding the outer lobes of the balloon 58, 60, 62 down around the inner lumen 64, placing a sleeve, for example a short length of tubing, snugly over the folded-down outer lumens of the balloon and inserting adhesive, for example by wicking the adhesive, around the entire inner circumference of the sleeve. The inner lumen is then fastened to the shaft using a second short length of tubing. The second short length for example 1 mm, of intermediate tubing 104 is heat welded to the inside of the inner lumen. The intermediate tube has an outer diameter approximately the same as the inner diameter of the inner lumen. The intermediate tube is then slid over the shaft at about the location of the neck-down region near the proximal marker 102, and adhesive 106 is wicked into the space between the inside of the intermediate tubing and the outer surface of the shaft 50. A similar process may be used to attach the distal end of the balloon, as will be described, except that the distal end of the balloon is attached down around the guide wire extension tube 98 rather than the shaft.

Just distal of the proximal balloon seal, under the balloon within the inner lumen, an elongated window 108 is cut through the wall of the outflow lumen in the shaft. Along the proximal portion of the balloon above this window, five slits, e.g. 110, are cut into the common wall between each of the outer lumens 58, 60, 62 and the inner lumen 64. Because the outer lumens are twined about the inner lumen in a helical fashion, each of the outer tubes passes over the outflow lumen of the inner shaft member at a slightly different location along the length of the inner shaft and, therefore, an elongated window 108 is cut into the outflow lumen of the shaft so that each outer lumen has at least one slit e.g. 110 that is located over the window in the shaft. Additionally, there is sufficient clearance between the outer surface of the shaft and the wall of the inner lumen to allow relatively unrestricted flow of heat exchange fluid through all 5 slits in each outer lumen, around the shaft, and through the elongate window 108 into the outflow lumen 54 in the shaft 50.

Distal of the elongated window in the outflow lumen, the inner lumen 64 of the four-lumen balloon is sealed around the shaft in a fluid tight plug. Referring to FIG. 10a, the plug is formed by, for example shrinking a relatively thick length of PET tubing to form a length of plug tubing 112 where the inner diameter of the length of plug tubing is approximately the same as the outer diameter of the shaft at the location where the plug is to be formed. The plug tubing is slid over the shaft and fits snugly against the shaft. The shaft is generally formed of a material that is not heat shrinkable. As may be seen in FIG. 10A and FIG. 3, some clearance exists between the outer wall of the shaft and the inner wall of the inner lumen 64. The walls of the inner lumen are composed of thin heat shrinkable material, for example PET. A probe with a resistance heater on the distal end of the probe is inserted into the guide wire lumen of the shaft and located with the heater under the plug tubing. The probe is heated, causing the heat shrink wall of the inner lumen to shrink down against the plug tubing, and the plug tubing to shrink slightly down against the shaft. The resultant mechanical fit is sufficiently fluid tight to prevent the outflow lumen and the space between the shaft and the wall of the inner lumen from being in fluid communication directly with the inner member or the inflow lumen distal of the plug except through the outer lumens as will be detailed below.

Just distal of the plug, the outflow lumen is closed by means of a heat seal 99, and the inflow lumen is skived to form an opening 101 to the inner member. This may be accomplished by necking down the shaft at 96, attaching a guide wire extension tube 98 to the guide wire lumen, and simultaneously opening the inflow lumen 101 to the interior of the inner lumen and heat sealing the outflow lumen shut 101. The guide wire extension tube continues through the inner lumen, beyond the distal seal of the balloon (described below) to the distal end of the catheter 114 and thereby creates communication between the guide wire port 80 and the vessel distal of the catheter for using a guide wire to place the catheter or for infusing drugs, radiographic dye, or the like beyond the distal end of the catheter.

The distal end of the balloon 76 is sealed around the guide wire extension tube in essentially the same manner as the proximal end 74 is sealed down around the shaft. Just proximal of the distal seal, five slits 116 are cut into the common wall between each of the three outer lumens 58, 60, 62 of the balloon and the inner lumen 64 so that each of the outer lumens is in fluid communication with the inner lumen.

Just distal of the balloon, near the distal seal, a distal marker band 118 is placed around the guide wire extension tube. A flexible length of tube 120 may be joined onto the distal end of the guide wire tube to provide a soft tip to the catheter as a whole.

In use, the catheter is inserted into the body of a patient so that the balloon is within a blood vessel, for example in the inferior vena cava (IVC). Heat exchange fluid is circulated into the inflow port 82, travels down the inflow lumen 52 and into the inner lumen 64 distal of the plug tube 112. The heat exchange fluid fills the inner lumen and travels down the inner lumen, thence through slits 116 between the inner lumen 64 and the three outer lumens 58, 60, 62.

Figure 3:
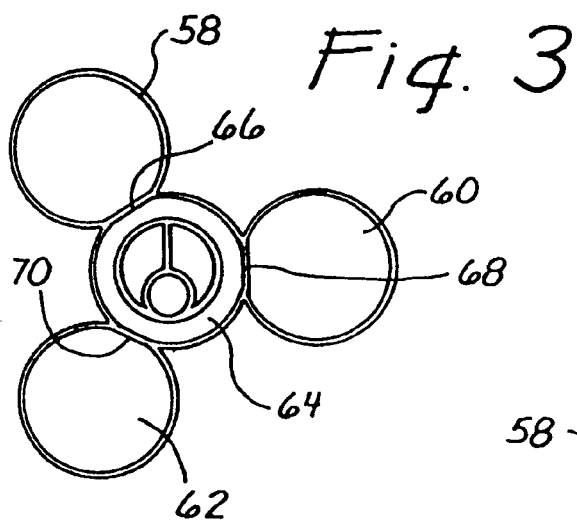
FIG. 3 is a cross-sectional drawing of the heat exchange region of the catheter taken along the line 3—3 in FIG. 1.
Figure 3A:
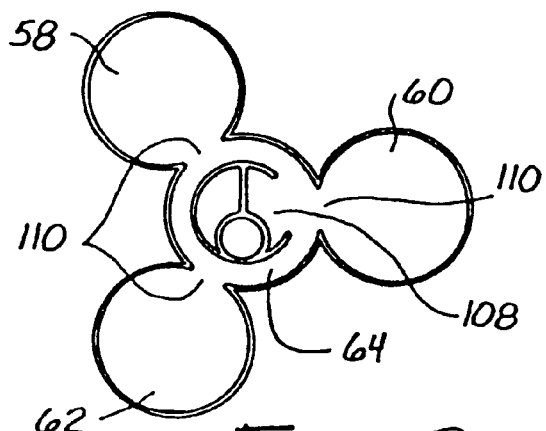
FIG. 3A is a cross-sectional view through line 3A—3A of FIG. 1.
Figure 5:
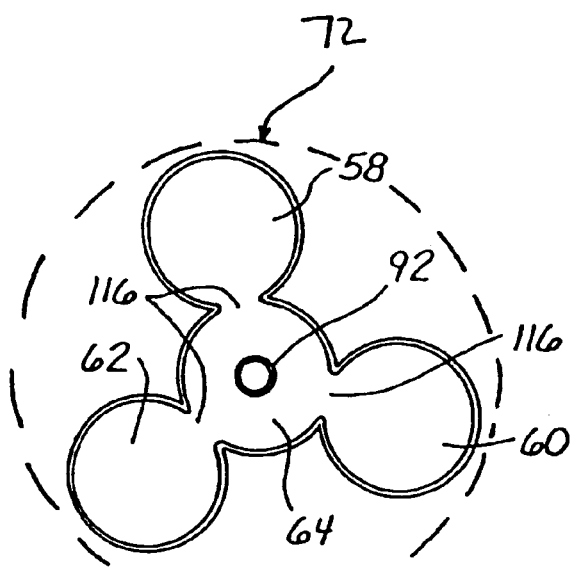
FIG. 5 is a cross-sectional drawing of the heat exchange region of the catheter taken along the line 5—5 in FIG. 1.
Figure 4:
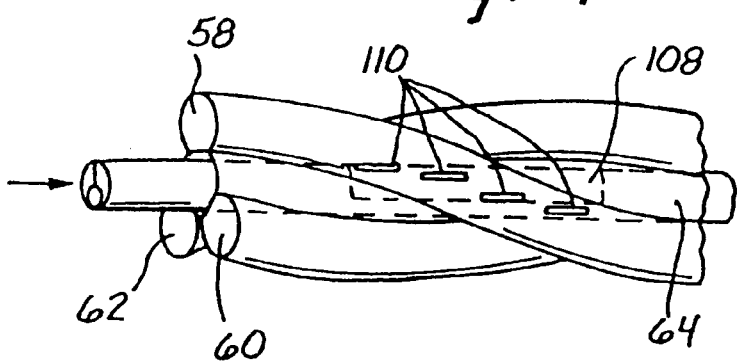
FIG. 4 is a perspective drawing of a segment of the heat exchange region of the catheter within the circle 4—4 in FIG. 1.

The heat exchange fluid then travels back through the three outer lumens of the balloon to the proximal end of the balloon. Since outer lumens are wound in a helical pattern around the inner lumen, at some point along the length of the balloon near the proximal end and proximal of the plug, each outer lumen is located over the portion of the shaft having the window to the outflow lumen 108. There is also sufficient clearance between the wall of the inner lumen and the shaft, as illustrated in FIG. 3, that even the slits that are not directly over the window 108 allow fluid to flow into the space between the wall of the inner lumen and the outer wall of the shaft 50 and then through the window 108 and into the outflow lumen. The heat exchange fluid then flows down the outflow lumen and out the outflow port 84. At a fluid pressure of 41 pounds per square inch, flow of as much as 500 milliliters per minute may be achieved with this design.

Counter-current circulation between the blood and the heat exchange fluid is highly desirable for efficient heat exchange between the blood and the heat exchange fluid. Thus if the balloon is positioned in a vessel where the blood flow is in the direction from proximal toward the distal end of the catheter, for example if it were placed from the femoral vein into the IVC, it is desirable to have the heat exchange fluid in the outer balloon lumens flowing in the direction from the distal end toward the proximal end of the catheter. This is the arrangement described above. It is to be readily appreciated, however, that if the balloon were placed so that the blood was flowing along the catheter in the direction from distal to proximal, for example if the catheter was placed into the IVC from a jugular insertion, it would be desirable to have the heat exchange fluid circulate in the outer balloon lumens from the proximal end to the distal end. Although in the construction shown this is not optimal and would result is somewhat less effective circulation, this could be accomplished by reversing which port is used for inflow direction and which for outflow.

Where heat exchange fluid is circulated through the balloon that is colder than the blood in the vessel into which the balloon is located, heat will be exchanged between the blood and the heat exchange fluid through the outer walls of the outer lumens, so that heat is absorbed from the blood. If the temperature difference between the blood and the heat exchange fluid (sometimes called "ΔT"), for example if the blood of the patient is about 37° C. and the temperature of the heat exchange fluid is about 0° C., and if the walls of the outer lumens conduct sufficient heat, for example if they are of very thin (0.002 inches or less) plastic material such as polyethylene terephthalate (PET), enough heat may be exchanged (for example about 200 watts) to cool the temperature downstream of the catheter, for example of the heart, sufficiently for therapeutic inotropic. If the cooling catheter is left in place long enough for example for over half an hour, the entire body temperature of the patient may be cooled sufficiently to reduce the metabolism of the rest of the body and reduce the demands placed on the heart.

The helical structure of the outer lumens has the advantage over straight lumens of providing greater length of heat exchange fluid path for each length of the heat exchange region. This creates additional heat exchange surface between the blood and the heat exchange fluid for a given length of balloon. It may also provide for enhanced flow patterns for heat exchange between flowing liquids. The fact that the heat exchange region is in the form of an inflatable balloon also allows for a minimal insertion profile, for example 9 French or less, while the heat exchange region may be inflated once inside the vessel for maximum surface area of the heat exchange region in operation.

Referring now to FIGS. 11 through 13B, in another example of a preferred embodiment, the heat exchange region is in the form of a series of five lumens arranged side-by-side in a configuration that may be loosely described as a twisted ribbon. The heat transfer fluid circulates to and from the heat exchange region 202 via channels formed in the shaft 206 in much the same manner as previously described for shaft 50. Indeed, although not depicted, the shaft has a similar internal configuration as the shaft previously described with an inflow lumen, an outflow lumen, and a working lumen. Although also not depicted, a hub is attached at the proximal end of the shaft, which is maintained outside the body; the hub has a guide wire port communicating with the working lumen, an inflow port communicating with the inflow lumen, and an outflow port communicating with the outflow lumen. Heat exchange fluid is directed into the catheter through the inflow port and removed from the catheter through the outflow port. A guide wire, or alternatively medicaments, radiographic fluid, small diameter medical device, or the like are introduced through the guide wire port and may thus be directed to the distal end of the catheter. When the catheter is in the IVC, the medicaments or the medical device may be delivered directly to the heart region.

Figure 11:
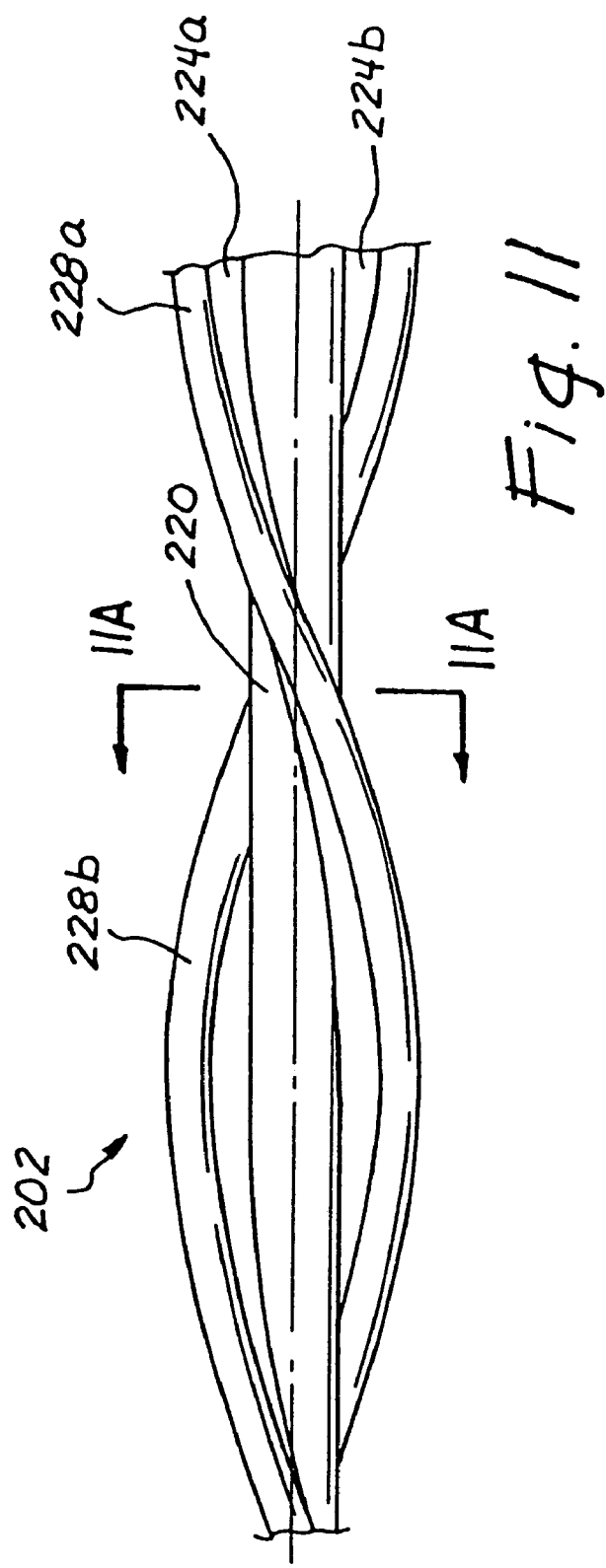
FIG. 11 is a perspective view of a portion of a multi-lobed, curvilinear heat exchange balloon that of a catheter that may be used in the invention.
Figure 11A:
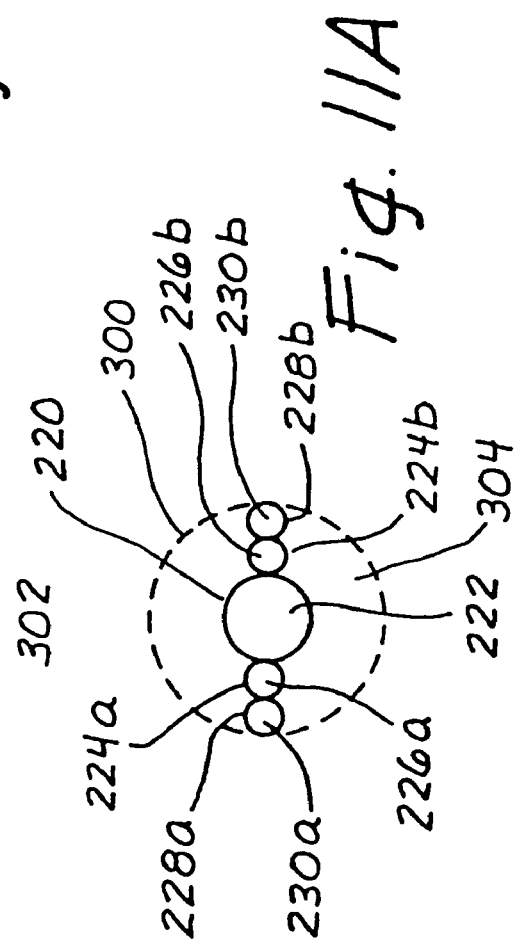
FIG. 11A is a cross sectional view of the heat exchange region taken along the line 11A—11A in FIG. 11.

FIGS. 11 and 11A illustrate this embodiment of a heat exchange region 202 comprising a plurality of tubular members that are stacked in a helical plane. More specifically, a central tube 220 defines a central lumen 222 therewithin. A pair of smaller intermediate tubes 224a, 224b attaches to the exterior of the central tube 220 at diametrically opposed locations. Each of the smaller tubes 224a, 224b defines a fluid lumen 226a, 226b therewithin. A pair of outer tubes 228a, 228b attaches to the exterior of the intermediate tubes 224a, 224b in alignment with the aligned axes of the central tube 220 and intermediate tubes 224a, 224b. Each of the outer tubes 228a, 228b defines a fluid lumen 230a, 230b within. By twisting the intermediate and outer tubes 224a, 224b, 228a, 228b around the central tube 220, the helical ribbon-like configuration of FIG. 11 is formed.

Now with reference to FIGS. 12 and 12A–12C, a proximal manifold of the heat exchange region 202 will be described. The shaft 206 extends a short distance, desirably about 3 cm, within the central tube 220 and is thermally or adhesively sealed to the interior wall of the central tube as seen at 250. As seen in FIG. 12A, the shaft 206 includes a planar bulkhead or web 252 that generally evenly divides the interior space of the shaft 206 into an inflow lumen 254 and an outflow lumen 256. A working or guide wire lumen 260 is defined within a guide wire tube 262 that is located on one side of the shaft 206 in line with the bulkhead 252. Desirably, the shaft 206 is formed by extrusion. The outflow lumen 256 is sealed by a plug 264 or other seal at the terminal end of the shaft 206. The inflow lumen 254 remains open to the central lumen 222 of heat exchange region 202. The guide wire tube 262 continues a short distance and is heat bonded at 270 to a guide wire extension tube 272 generally centered within the central tube 220.

A fluid circulation path is illustrated by arrows in FIG. 12 and generally comprises fluid passing distally through the inflow lumen 254 and then through the entirety of the central lumen 222. The heat exchange fluid is directed from the central lumen 222 to the intermediate and outer tubes as will be described below, and returns through the lumens 226a, 226b, and 230a, 230b of the intermediate and outer tubes 224a, 224b, and 228a, 228b, respectively, and enters reservoirs 274 and 275. Alternatively, two windows may be formed 276 and a counterpart not shown in FIG. 12 one helical twist farther down the shaft, between each side of the twisted ribbon (i.e., lumens 224*a* and 224*b* on one side, and 228*a* and 228*b* on the other side). In this way, one reservoir from each side of the twisted ribbon is formed in fluid communication with the outflow lumen 256 (configuration not shown). Fluid then enters the outflow lumen 256 through apertures, e.g., 276, provided in the central tube 220 and a longitudinal port 278 formed in the wall of the shaft.

A distal manifold of the heat exchange region 202 is shown and described with respect to FIGS. 13 and 13A–13B. The outer tubes 228*a*, 228*b* taper down to meet and seal against the central tube 220 which, in turn, tapers down and seals against the guide wire extension tube 272. Fluid flowing distally through the central lumen 222 passes radially outward through a plurality of apertures 280 provided in the central tube 220. The apertures 280 open to a distal reservoir 282 in fluid communication with lumens 226*a*, 226*b*, and a distal reservoir 281 in fluid communication with lumens 230*a*, 230*b* of the intermediate and outer tubes 224*a*, 224*b*, and 228*a*, 228*b*.

With this construction, heat exchange fluid introduced into the input port 240 will circulates through the inflow lumen 254, into the central lumen 222, out through the apertures 280, and into the distal reservoir 282. From there, the heat exchange fluid will travel proximally through both intermediate lumens 226*a*, 226*b* and outer lumens 230*a*, 230*b* to the proximal reservoirs 274 and 275. Fluid then passes radially inwardly through the apertures 276 and port 278 into the outflow lumen 256. Then the fluid circulates back down the shaft 206 and out the outlet port 242.

The ribbon configuration of FIGS. 11–13B is advantageous for several reasons. First, the relatively flat ribbon does not take up a significant cross-sectional area of a vessel into which it is inserted. The twisted configuration further prevents blockage of flow through the vessel when the heat exchange region 202 is in place. The helical configuration of the tubes 224*a*, 224*b*, 228*a*, 228*b* also aids to center the heat exchange region 202 within a vessel by preventing the heat exchange region from lying flat against the wall of the vessel along any significant length of the vessel. This maximizes heat exchange between the lumens and the blood flowing next to the tubes. Because of these features, the twisted ribbon configuration is ideal for maximum heat exchange and blood flow in a relatively small vessel such as the IVC of a very small patient such as a pediatric patient. As seen in FIG. 11A, an exemplary cross-section has a maximum diameter of about 5 mm, permitting treatment of relatively small vessels. The helical pattern of the balloon in the fluid flow may act to induce a gentle mixing action of the flowing blood to enhance heat exchange between the heat exchange surface and the blood without inducing hemolytic damage that would result from more violent churning action.

The deflated profile of the heat exchange region is small enough to make an advantageous insertion profile, as small as 7 French for some applications. Even with this low insertion profile, the heat exchange region is efficient enough to adequately exchange heat with blood flowing past the heat exchange region to alter the temperature of the blood sufficient for the inotropic effect and decreased metabolic demands along with tissue protection for the heart.

This configuration has a further advantage when the heat exchange region is placed in a tubular conduit such as a blood vessel, especially where the diameter of the vessel is approximately that of the major axis (width) of the cross section of the heat exchange region. The configuration tends to cause the heat exchange region to center itself in the middle of the vessel. This creates two roughly semicircular flow channels within the vessel, with the blood flow channels divided by the relatively flat ribbon configuration of the heat exchange region. It has been found that the means for providing maximum surface for heat exchange while creating minimum restriction to flow is this configuration, a relatively flat heat exchange surface that retains two approximately equal semi-circular cross-sections. This can be seen in reference to FIG. 11A if the functional diameter of the dashed circle 300 is essentially the same as the luminal diameter of a vessel into which the twisted ribbon is placed. Two roughly semi-circular flow paths 302, 304 are defined by the relatively flat ribbon configuration of the heat exchange region, i.e. the width or major axis (from the outer edge of 228*a* to the outer edge of 228*b*) is at least two times longer than the height, or minor axis (in this example, the diameter of the inner tube 222) of the overall configuration of the heat exchange region. It has been found that if the heat exchange region occupies no more than about 50% of the overall cross-sectional area of the circular conduit, a highly advantageous arrangement of heat exchange to flow is created. The semi-circular configuration of the cross-section of the flow channels is advantageous in that, relative to a round cross-sectioned heat exchange region (as would result from, for example, a sausage shaped heat exchange region) the flow channels created minimize the surface to fluid interface in a way that minimizes the creation of laminar flow and maximizes mixing. Maximum blood flow is important for two reasons. The first is that maximum blood flow downstream to supply blood to the tissue is important, especially if the heart is already compromised. The second reason is that heat exchange is highly dependent on the rate of blood flow past the heat exchange region, with the maximum heat exchange occurring with maximum blood flow, so maximum blood flow is important to maximizing heat transfer.

Control of Patient Temperature

Automated control of the endovascular process is optional. Examples of apparatus and techniques that may be used for automated control of the process are described in U.S. Pat. Nos. 6,149,676 and 6,149,676 and co-pending U.S. patent applications Ser. Nos. 09/138,830, 09/563,946 and 09/707,257 the entireties of which are expressly incorporated herein by reference.

Figure 15:
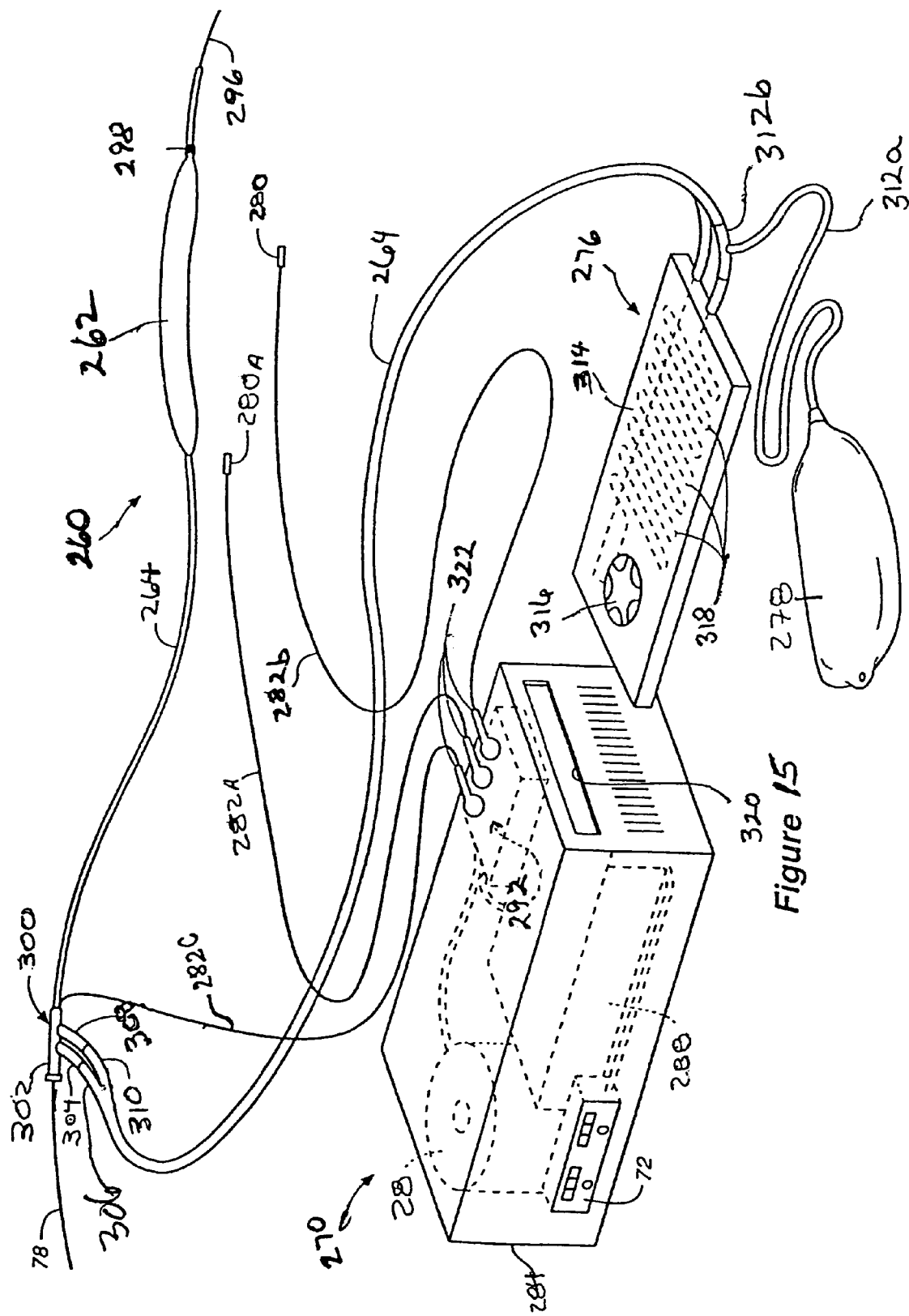
FIG. 15 is a depiction of a catheter and controller for practicing the invention.

The general use of temperature feedback from a patient to control endovascular cooling is illustrated in FIGS. 14 and 15. A cooling catheter 260 having a heat exchange region 262 is placed using the well known Seldginger technique so that the shaft 264 is located in the femoral vein and advanced so that the heat exchange region is located in the IVC. The catheter may use the flow of a heat exchange fluid for heat exchange, as was described in the section above. The temperature of the heat exchange fluid is controlled by an external heat exchanger 268 and a control unit 270 may control the temperature of the external heat exchanger. The control unit in turn receives a signal transmitted from a temperature sensor 272 in the heart 274 of the patient. The temperature sensor shown is a heart temperature probe, but other temperature sensors are certainly contemplated by this method. The temperature sensors generally should provide an accurate measure that represents the temperature of the heart which generally includes any measure of core temperature such as a tympanic temperature sensor, an esophageal temperature probe, a needle probe located in the patient's thigh, a bladder probe or the like. The probe should provide a signal that can be utilized for providing useful information to the controller, for example an electric signal from a thermistor.

A more detailed illustration of this method of controlling the heat exchange catheter is illustrated in FIG. 15. In an exemplary embodiment, FIG. 15 illustrates a heat exchange catheter system that includes a re-usable catheter control unit 270 and a plurality of disposable components including a heat exchange catheter 260, an external heat exchange element 276, a saline bag 278, sensors 280a, 280b and associated wires 282a, 282b, and a plurality of fluid flow conduits including a two-way conduit 264 extending distally from the heat exchange element 276. The re-usable catheter control unit 270 includes an outer housing 284 within which is provided a heater/cooler 288, a pump driver 290, and a controller processor 292. In addition, a manual input unit 294 enables an operator to enter desirable operating parameters of the controller, for example a pre-selected core temperature. Each of the electronic devices provided within the control unit 270 communicate through suitable wiring.

The heat exchange catheter 260 is formed with a catheter shaft 264 that functions as a flow line and a heat exchanged region 262 that may be, for example, a heat exchange balloon operated using a closed-loop flow of a biocompatible fluid that serves as the heat exchange medium. The catheter 260 may include a working lumen (not shown) for injection of drugs, fluoroscopic dye, or the like, and for receipt of a guide wire 296 for use in placing the catheter at an appropriate location in the patient's body, or other small diameter medical device. A sensor 298 may be provided on the catheter 260 distal to the heat exchange region 262 to monitor the temperature of the heat exchange balloon, and other sensors (not shown) may be provided as desired to monitor the blood temperature at the distal tip of the catheter, at the proximal tip of the balloon, or at any other desired location along the catheter.

The proximal end of the catheter flow line 264 may be connected to a multi-arm adapter 300 for providing separate access to various channels in the catheter 260. For example, a first arm 302 may provide access to the working lumen of the catheter 260 for insertion of the guide wire 296 to steer the heat exchange catheter to the desired location. Where the heat exchange region 262 is a heat exchange balloon for closed-loop flow of a heat exchange medium, the adapter 300 may contain a second arm 304 connected to an inflow line 306, and a third arm 308 connected to an outflow line 310. The inflow line 306 and outflow line 310 are therefore placed in flow communication with respective inflow and outflow channels (not shown) provided in the flow line 264 and heat exchange region 262. In this regard, the inflow and outflow lines 306, 310 may come together to form the single dual channel flow line 264 connected to the heat exchange element 276. Furthermore, an external fluid source such as the saline bag 278 may be placed in fluid communication with the outflow line 310 via a conduit 312a and a T-junction 312b. As will be explained further below, the external fluid source is used to prime the closed-loop heat exchange balloon system. Alternatively, the external fluid source may be directly connected to the heat exchange unit 276.

Still with reference to FIG. 15, the heat exchange unit 276 desirably includes a heat exchange plate 314 and a pump head 316. The pump head 316 pumps heat exchange fluid through a serpentine fluid pathway 318 in the heat exchange plate 314, and through the associated flow lines and catheter 260. As mentioned, the heat exchange unit 276 is configured to install into the re-usable catheter control unit 270. In this regard, the heat exchange unit 276 is desirably plate-shaped and sized to fit through an elongate slot 320 in the control unit housing 284. Once inserted, the pump head 316 is placed in proximity to and engaged with the pump driver 290, and the heat exchange plate 314 is placed in proximity to and in thermal communication with the heater/cooler 288. A solid-state thermoelectric heater/cooler 288 is particularly advantageous because the same unit is capable of either generating heat or removing heat by simply changing the polarity of the current activating the unit. Therefore, the heater/cooler 288 may be conveniently controlled so as to supply or remove heat from the system without the need for two separate units.

The pump driver 290 engages and activates the pump head 316 to cause it to circulate heat exchange fluid through the heat exchange unit 276 and the serpentine path 318 in the heat exchange plate 314. Therefore, when the heat exchanger unit 276 is properly installed in the control unit 270, the heater/cooler 288 may act to heat or cool the heat exchange fluid as that fluid is circulated through the serpentine pathway 318 and thereafter through the flow lines leading to the in-dwelling heat exchange region 262. When the heat exchange fluid is circulated through the heat exchange region 262 located in the patient's body, it may act to add or remove heat from the body. In this way, the heater/cooler 288 regulates the blood temperature of the patient as desired.

The heater/cooler 288 and a pump driver 290 are responsive to the controller processor 292. The processor 292 receives data input through electrical connections 322 to numerous sensors, for example body temperature sensors 280a, 280b positioned to sense the temperature at various locations within the patient. For example, the temperature may be sensed at the patient's ear, heart region, bladder, rectum, esophagus, upper thigh or other appropriate location as desired by the operator. Also, as mentioned, a sensor 298 may monitor the temperature of the heat exchange region 262, and other sensors along the catheter 260 may provide input to the controller processor 292, such as via a wire 282c. Additionally, by means of the manual input unit 294, an operator provides the operating parameters of the control system such as, for example, a pre-selected temperature for the heart and/or the whole body of the patient. The operator input parameters are communicated to the controller processor 292 by means of appropriate wiring.

The controller processor 292 coordinates the various data received and selectively actuates the several operational subsystems to achieve and maintain desired results; i.e., proper regulation of the patient's body temperature. For example, the processor 292 may actuate the heater/cooler 288 to increase the amount heat it is removing if the actual temperature is above the specified temperature, or it may decrease the amount of heat being removed if the temperature is below the specified temperature. Alternatively, the processor 292 may control the speed of the pumping of the heat exchange fluid in response to the sensed body or regional temperature.

Referring still to FIG. 15, the disposable heat exchange unit 276 of the invention is shown as being attached to a heat exchange catheter 260, external fluid source 278 is positioned in cooperation with a suitable reusable master control unit 270. Prior to commencing treatment, the heat exchange unit 276 is inserted into the reusable master control unit 270, the external fluid source 278 is attached to the fill port and the pump 316 is automatically or passively primed and the disposable system filled, after which the catheter is ready for insertion in the vasculature of the patient, for example in the inferior vena cava or other suitable vessel. Chilled or warmed biocompatible fluid such as saline, is pumped into the closed circuit catheter, which exchanges heat directly with the patient's blood. The control unit serves to automatically control the patient's temperature. Once treatment with the catheter is complete, the catheter is removed from the patient and the cassette is removed from the reusable master control unit. Both the catheter and cassette may then be discarded. The reusable master control unit, however, which never comes into direct contact with the heat exchange fluid, is ready for immediate use for treatment on other patients, along with a new cassette and catheter and fresh external fluid source.

Anti-Shivering Mechanism

As previously mentioned, if the patient is cooled below the shivering threshold (generally about 35.5° C.) some mechanism must be used to combat shivering. Methods of combating shivering while cooling a patient are described in detail in U.S. Pat. No. 6,231,594 to Dae et al. that is incorporated in its entirety herein by reference. For example, if a patient is cooled below his or her shivering threshold, which is the temperature at which a patient, absent application of anti-shivering mechanism, would shiver (which varies for each patient, but generally is about 35.5° C.), then a warming blanket might be applied, alone or in conjunction with various anti-shivering drugs. A typical therapeutic regime would comprise the steps of:

(i) administering an initial bolus dose of a first anti-thermoregulatory response agent to the patient (for example an oral dose of a serotonin 5 HT1a receptor agonist such as 60 mg of buspirone);

(ii) administering a subsequent dose of a second anti-thermoregulatory response agent to the patient (for example an initial intravenous dose of an μ opioid receptor agonist such as 50 mg of meperidine administered by slow push followed by a similar second dose); and (iii) administering a further dose of the second anti-thermoregulatory response agent by constant IV administration (for example, constant IV administration of about 25 mg/hr of meperidine).

A warming blanket is wrapped around the patient as soon as possible, usually about the time the first anti-thermoregulatory response agent is administered. As soon as the physician believes that the anti-thermoregulatory response mechanism is operating, the cooling catheter is placed and cooling is begun.

Another similar regime may be practiced to suppress shivering in a patient maintained below the shivering threshold for a longer period.

(i) administering a first dose of an anti-thermoregulatory response agent to the patient (for example an intravenous dose of an μ opioid receptor agonist such as 50 mg of meperidine administered by slow push and infused over about 5 minutes);

(ii) administering a second dose of the anti-thermoregulatory response agent to the patient (for example, about 15 minutes after the initial administration of meperidine, an additional 50 mg of meperidine is administered by slow IV push);

(iii) administering a third dose of the anti-thermoregulatory response agent by constant IV administration (for example, constant IV administration of about 25 mg/hr of meperidine maintained for the duration of the time that the patient's temperature is below the shivering threshold);

(iv) an intravenous temperature control catheter of the general type described above is introduced into the vasculature of the patient and the heat exchange region of the catheter is placed in the IVC and cooling is begun at the maximum rate. The patient is thereafter maintained at a therapeutically low temperature even below the shivering threshold.

A warming blanket may be applied to the patient before the drug regime is begun, or after the drug regime is begun, and generally is maintained for the duration of the time the patient is below the shivering threshold. Application of warmth to the patient's face is generally particularly effective.

Another anti-shivering drug that may be particularly useful is dexmedetomidine.

Examples of the Method of the Invention

A. Cooling a Patient with Mild Cardiac Insufficiency

A patient who has not yet fallen into severe congestive heart failure may non-the-less benefit from a period of inotropic hypothermia. For example, a patient who has begun to slip into what is described as compensated CHF or symptomatic CHF may be administered a period of inotropic hypothermia that may increase the heart function sufficiently and improve the overall vascular condition of the patient to restore that patient to the asymptomatic condition for some period of time and thus delay or prevent the more serious deterioration of the patient's condition and improve the patient's overall quality of life.

The method would comprise the steps of:

(i) begin the application of anti-shivering mechanisms, generally comprising the application of anti-shivering drugs and the application of a warming blanket. The warming blanket may not be turned on or may be turned on low at the outset, and the power of the blanket increased as the patient's temperature is lowered.

(ii) insert the endovascular cooling catheter and begin cooling to a desired temperature, for example about 32° C. Depending on the condition of the patient and the therapeutic response, the temperature may be significantly higher, for example 35° C., but will usually not go below 30° C. since the heart begins to be sensitive and irritable below that temperature.

(iii) control the patient's temperature at a desired level for a length of time sufficient to provide significant vascular benefit. For example the patient's temperature may be controlled by maintaining the desired temperature of 32° C. within 0.2° C. for several hours, usually more than 4 hours and sometimes more than one day. During this time the patient's condition would be monitored, both to identify and respond to any problem, for example to increase the patient's temperature if he or she begins to exhibit symptoms that will be relieved by increases in body temperature, and to follow the patient's response to treatment to keep the length of cooling as short and mild as possible to minimize the use of anti-shivering drugs. For example, if the patient exhibited the full beneficial response at 35° C. and was able to be maintained at that temperature without shivering using only a heating blanket on high and few or no anti-shivering drugs, that might be preferable.

(iii) slowly re-warm the patient to normothermia (usually 37° C.) using controlled re-warming. For example, re-warming at the rate of 0.2° C. may avoid injury that might occur with too rapid re-warming. Depending on the condition of the patient and the disease state addressed, re-warming at some other rate, for example 0.4° C. per hour, half a degree an hour or even a degree or more an hour might be appropriate.

B. Cooling a Patient with Late Stage Chronic Congestive Heart Failure

When a patient has reached the stage of heart disease sometimes called symptomatic CHF, application of hypothermia may be beneficial to improve th4e patient's condition to allow the heart to be restored to a healthier condition. If the patient is in refractory CHF it may be used to prolong that patient's life until a heart for heart transplantation becomes available. In such a case, the patient would be treated using the method described in the previous section A, except that the therapy would generally be repeated periodically, for example every few days or weeks as medically appropriate. Since hypothermia, unlike inotropic drugs, would not increase the metabolic by-products and is generally not toxic and does not induce tolerance and ineffectiveness of the treatment, it may be repeated more frequently and over a longer period than the inotropic drug holidays that would otherwise be provided to the patient.

C. Cooling a Patient with Post Operative Cardiac Failure

Sometimes a patient after surgery suffers cardiac failure and is unresponsive to inotropic drugs, or the application of those drugs is contra-indicated because of other drugs administered to the patient or because of the general condition of the patient. In those cases, the patient's vascular condition may be improved, essentially reviving the patient's heart to allow post-operative recovery. The method comprises:

(i) inserting the endovascular cooling catheter into the vasculature of the patient. This is then attached to the controller as described above.

(ii) if the patient is still under anesthesia and on a ventilator, no anti-shivering mechanisms need be applied. If not, then there should be the application of a warming blanket first and then any appropriate anti-shivering drugs;

(iii) cool the patient while monitoring the heart rate and cardiac output;

(iv) soon after the heart rate and cardiac output are sufficient in the physician's opinion, begin re-warming the patient. In this situation, the re-warming is generally faster than in the previously discussed situations since hypothermia may result in mild coagulopathies and a patient just out of surgery generally should be re-warmed to normothermia as soon as the heart is pumping adequately.

D. Stabilizing a Patient for Cardiac Intervention or Surgery

Many times, a patient is not a candidate for needed cardiac surgery or intervention because of poor cardiovascular condition. Before the patient can be treated with the needed surgery or intervention, their cardiac condition must be improved and stabilized. Often the improvement is effected by drug therapy using inotropic drugs, and a ventricular assist device or an aortic balloon pump may be employed. This invention adds the application of hypothermia to this armament. The hypothermia is adjunctive to each of these therapies and does not eliminate the availability of any of them.

The method is similar to that described above. The patient is cooled to provide inotropic hypothermia. If the patient is cooled below the shivering threshold, anti-shivering methods are generally applied. Since the endovascular heat exchange catheter is generally located with the heat exchange region in the IVC, it would not interfere with devices used in the aorta. For example, a left ventricular assist devices or an intra-aortic balloon pump may be employed. Similarly the angioplasty balloon is generally inserted into the cardiac arteries through the aorta and would not be interfered with by the heat exchange catheter. Hypothermia at the levels indicated do not seriously impair the functioning of inotropic drugs, so these too may be employed, although the treatment strategy generally when attempting to stabilize the heart prior to intervention is to rest the heart muscle as much as possible; often the heart muscle are then able to recover and become more stable and generally healthier. Stimulating it with inotropic drugs is contrary to this strategy, although using hypothermia is not.

Once the heart is sufficiently stable, the patient may undergo needed surgery or intervention. This may include, for example, percutaneous cardiac intervention (PCI), bypass surgery, left ventricular reduction surgery, cryoablation, or other similar surgery. The patient is generally maintained on hypothermia during the surgery or intervention, since the hypothermia is both inotropic and tissue protective. In this way, the heart function will be improved, and the heart and neural tissues will be protected with the hypothermia. After the surgery or intervention, the patient may be maintained at a hypothermic level for some time, for example three hours, and then slowly and controllably warmed back to normothermia, for example at 0.5° C. per hour.

While the present invention has been described with reference to the specific embodiments thereof, it should be understood by those skilled in the art that various changes may be made and equivalents may be substituted without departing from the scope of the invention. In addition, many modifications may be made to adapt a particular situation, material, composition of matter, process, process step or steps, while remaining within the scope of the present invention. Accordingly, the scope of the invention should therefore be determined with reference to the appended claims, along with the full range of equivalents to which those claims are entitled.

What is claimed is:

1. A method of treating cardiac failure in a human or veterinary patient, said method comprising the steps of:
   a) cooling the patient's heart to a temperature that is at least 1° C. below normothermia; and,
   b) maintaining the temperature of the patient's heart at least 1° C. below normothermia for a sufficient period of time to provide improved cardiac output.

2. The method of claim 1 wherein steps a and b are carried out at least in part by i) inserting a cooling catheter into the patient's vasculature, said cooling catheter having a heat exchange region and a core, said heat exchange region thermally coupled to said core, the cooling catheter being positioned within the patient's vasculature such that the heat exchange region is positioned in the lumen of a blood vessel, the inner diameter of the blood vessel lumen being larger than the outer diameter of said heat exchange region, and ii) exchanging heat between blood flowing past said heat exchange region and said heat exchange region for sufficient time to cool the patient's heart tissue to a temperature at least 1° C. less than normothermia.

3. The method of claim 2 wherein the heat exchange region of the cooling catheter comprises a heat exchange balloon through which a heat exchange fluid is circulated.

4. The method of claim 3 wherein the heat exchange balloon comprises a plurality of balloon lobes disposed in a generally helical configuration.

5. The method of claim 3 wherein said core comprises flowing heat exchange fluid.

6. The method of claim 2 wherein the cooling catheter is positioned such that its heat exchange region is in the inferior vena cava of the patient.

7. The method of claim 2 wherein steps a and b are carried out by circulating heat exchange fluid through an external heat exchanger to alter or maintain the temperature of said heat exchange fluid and through the catheter core to exchange heat between the heat exchange fluid and the patient's circulating blood.

8. The method of claim 1 wherein the patient's heart is cooled to a temperature below 35.5° C.

9. The method of claim 1 wherein an anti-shivering treatment is administered to prevent the patient from shivering.

10. The method of claim 9 wherein the anti-shivering treatment includes one or more of the anti-shivering mechanisms selected from the group consisting of:
   a) a warming blanket;
   b) busparone
   c) meperidine; and
   d) dexamedetomidine.

11. The method of claim 1 wherein the patient's heart is cooled for a period of at least three hours.

12. The method of claim 1 wherein the method is performed to stabilize the patient's condition prior to performance of an interventional medical procedure or surgery.

13. The method of claim 1 wherein the method is performed to treat a patient with mild cardiac failure.

14. The method of claim 1 wherein the method is performed to treat a patient with late stage chronic congestive heart failure.

15. The method of claim 1 wherein the method is performed to treat a patient with post operative cardiac failure.

16. The method of claim 1 further comprising the step of:
   d) placing a temperature probe in or on the patient to sense the temperature of part of a patient and to generate a temperature signal based on said sensed temperature, and controlling the patient temperature based on said temperature signal.

17. The method of claim 1 wherein step b comprises maintaining the patient's heart at a temperature at or below 36° C. for at least ½ hour.

* * * * *